(12) United States Patent
Fujita et al.

(10) Patent No.: US 8,791,261 B2
(45) Date of Patent: Jul. 29, 2014

(54) POLYHEDRAL TRANSITION METAL COMPLEX, TRANSITION METAL COMPLEX CONTAINING ULTRAFINE PARTICLES THEREIN, AND PROCESS FOR PRODUCING SAME

(75) Inventors: Makoto Fujita, Tokyo (JP); Sota Sato, Tokyo (JP); Kosuke Suzuki, Tokyo (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 373 days.

(21) Appl. No.: 13/255,739

(22) PCT Filed: Mar. 10, 2010

(86) PCT No.: PCT/JP2010/054008
§ 371 (c)(1),
(2), (4) Date: Nov. 30, 2011

(87) PCT Pub. No.: WO2010/104113
PCT Pub. Date: Sep. 16, 2010

(65) Prior Publication Data
US 2012/0095196 A1 Apr. 19, 2012

(30) Foreign Application Priority Data
Mar. 11, 2009 (JP) ................. 2009-058194

(51) Int. Cl.
*C07F 15/00* (2006.01)
*C07H 23/00* (2006.01)

(52) U.S. Cl.
USPC ............................................ 546/2; 536/17.1

(58) Field of Classification Search
USPC ........................................ 546/2; 536/8, 17.1
See application file for complete search history.

(56) References Cited

FOREIGN PATENT DOCUMENTS

| JP | 2000-086682 A | 3/2000 |
|---|---|---|
| JP | 2000-086683 A | 3/2000 |
| JP | 2003-055271 A | 2/2003 |
| JP | 2004-155660 A | 6/2004 |
| JP | 2005-075751 A | 3/2005 |
| JP | 2005-255545 A | 9/2005 |
| JP | 2006-248819 A | 9/2006 |
| JP | 2007-015947 A | 1/2007 |
| JP | 2008-214294 A | 9/2008 |

OTHER PUBLICATIONS

Fujita, Makoto et al., "A Molecular Lock," Journal of American Chemical Society, 1995, p. 4175-4176, vol. 117.
International Search Report of PCT/JP2010/054008, mailing date May 25, 2010.
Jung, Jong Hwa et al., "Sol-gel Transcription of Novel Sugar-based Superstructures Composed of Sugar-integrated Gelators Into Silica: Creation of a Lotus-shaped Silica Structure," Chem. Communication, 2000, p. 2343-2344.
Kamiya, Nozomi et al., "Saccharide-Coated M12L24 Molecular Spheres That Form Aggregates by Multi-interaction with Proteins," Journal of American Chemical Society, 2007, p. 3816-3817, vol. 129.
Shchipunov, Yurii et al., "Hybrid Polysaccharide-Silica Nanocomposites Prepared by the Sol-Gel Technique," Langmuir, 2004, p. 3882-3887, vol. 20.
Suzuki, Kosuke et al., "Synthesis of Monodisperse Silica Nanoparticles Within Coordination Hollow Spheres," Polymer Preprints, 2009, 2C-16, pp. 2903-2904, vol. 58.
Suzuki, Kosuke et al., "Template Synthesis of Precisely Monodisperse Silica Nanoparticles Within Self-Assembled Organometallic Spheres," Nature Chemistry, 2009, p. 25-29, vol. 2.

*Primary Examiner* — Charanjit Aulakh
(74) *Attorney, Agent, or Firm* — Westerman, Hattori, Daniels & Adrian, LLP

(57) ABSTRACT

Provided is a polyhedral transition metal complex including a hollow shell, the hollow shell including n1 (where n1 is an integer from 6 to 60) transition metal atoms and 2(n1) bidentate organic ligands, the bidentate organic ligands including a group derived from a polyhydroxy compound via a linking group, and formed so that the group derived from the polyhydroxy compound is oriented toward an inner space of the hollow shell. Also provided are: an ultrafine particle-containing transition metal complex including the polyhedral transition metal complex, and ultrafine particles of a metal oxide, the ultrafine particles being included within the hollow shell of the polyhedral transition metal complex; a method of producing the same. The invention thus provides a polyhedral transition metal complex that makes it possible to efficiently produce metal oxide particles having a uniform particle size of several nanometers, an ultrafine particle-containing polyhedral transition metal complex in which metal oxide particles are included within a polyhedral structure and the method of producing the same.

10 Claims, 8 Drawing Sheets

4.5 nm (2) +Si(OMe)₄ 72 eq.

(2) +Si(OMe)₄ 96 eq.

F I G. 9
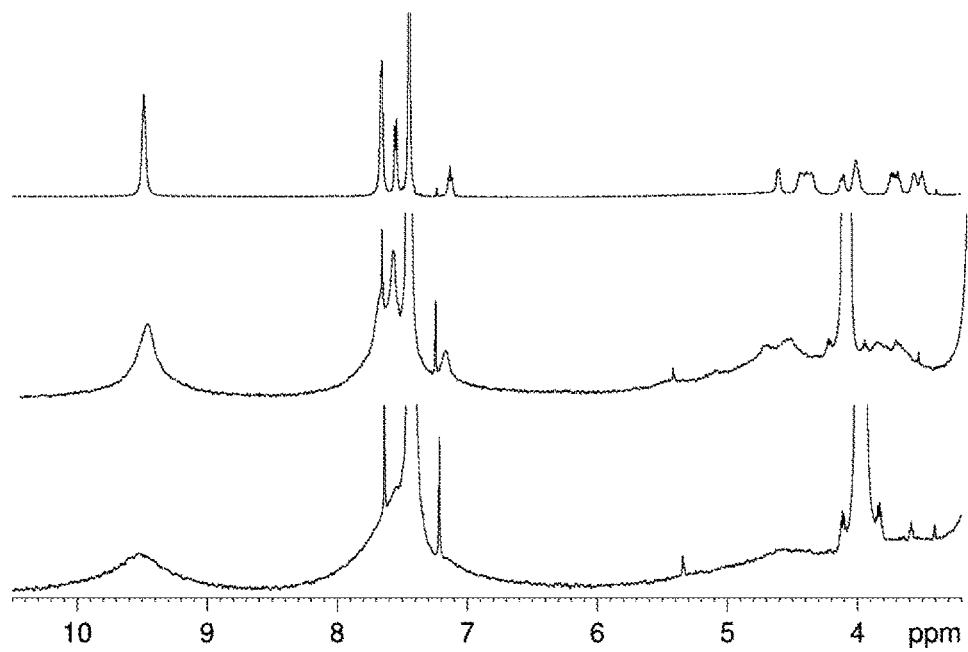

POLYHEDRAL TRANSITION METAL COMPLEX, TRANSITION METAL COMPLEX CONTAINING ULTRAFINE PARTICLES THEREIN, AND PROCESS FOR PRODUCING SAME

TECHNICAL FIELD

The present invention relates to a polyhedral transition metal complex that is formed by a transition metal atom and a bidentate organic ligand that includes a polyhydroxy compound via a linking group, an ultrafine particle-containing transition metal complex that includes ultrafine metal oxide particles within the hollow shell of the polyhedral transition metal complex, and a method of producing the same.

BACKGROUND ART

It is known that when molecules or atoms (ions) are confined in an isolated three-dimensional space formed by other molecules, the molecules or atoms (ions) show a specific behavior. Attempts have been made to improve reactivity, membrane permeability, and the like by utilizing such a phenomenon.

The present inventors established a method that efficiently produces a hollow metal complex that includes an isolated three-dimensional space in the molecule, and have developed technology that utilizes the hollow metal complex (see Non-patent Document 1 and Patent Documents 1 to 5, for example).

Non-patent Document 2 discloses that a polysaccharide functions as a catalyst for a polycondensation reaction (sol-gel polymerization) of a silicon alkoxide such as tetra(2-hydroxyethoxy)silane (THEOS). Non-patent Document 3 discloses that a lotus-shaped silica structure is obtained by a sol-gel reaction of tetraethoxysilane (TEOS) using a sugar compound as a template.

RELATED-ART DOCUMENT

Patent Document

Patent Document 1: JP-A-2000-86682
Patent Document 2: JP-A-2000-86683
Patent Document 3: JP-A-2003-55271
Patent Document 4: JP-A-2005-75751
Patent Document 5: JP-A-2005-255545

Non-Patent Document

Non-patent Document 1: J. Am. Chem. Soc., 117, 4175 (1995)
Non-patent Document 2: Langmuir, 2004, 20 (10), 3882-3887
Non-patent Document 3: Chem. Commun., 2000, 2343-2344

SUMMARY OF THE INVENTION

Problems to be Solved by the Invention

Metal oxide particles such as silica microparticles have been utilized in various applications such as a polishing agent, a coating agent, and a catalyst carrier. However, it has been difficult to produce particles having a uniform particle size of several nanometers.

An object of the invention is to provide a polyhedral transition metal complex that makes it possible to efficiently produce metal oxide particles having a uniform particle size of several nanometers, an ultrafine particle-containing transition metal complex that includes ultrafine metal oxide particles within the hollow shell of the polyhedral transition metal complex, and a method of producing the same.

Means for Solving the Problems

The inventors synthesized 2-[2,6-bis(4-pyridylethynyl)phenoxy]ethyl 2,3,4,6-tetra-O-acetyl-D-glucopyranoside and the like, and successfully synthesized a polyhedral transition metal complex using such a compound as a bidentate organic ligand. The inventors found that a metal alkoxide (e.g. tetramethoxysilane) added to the polyhedral transition metal complex enters the hollow shell of the polyhedral transition metal complex, and undergoes a polycondensation reaction, so that a complex that includes ultrafine metal oxide particles (ultrafine particle-containing transition metal complex) can be efficiently obtained. This finding has led to the completion of the invention.

A first aspect of the invention provides the following polyhedral transition metal complex (see (i) to (viii)).

(i) A polyhedral transition metal complex including a hollow shell, the hollow shell including n1 (where n1 is an integer from 6 to 60) transition metal atoms and 2(n1) bidentate organic ligands, the bidentate organic ligands including a group derived from a polyhydroxy compound via a linking group, and formed so that the group derived from the polyhydroxy compound is oriented toward an inner space of the hollow shell.

(ii) A polyhedral transition metal complex including a hollow shell, the hollow shell including n2 (where n2 is 6, 12, 24, 30, or 60) transition metal atoms and 2(n2) bidentate organic ligands, the bidentate organic ligands including a group derived from a polyhydroxy compound via a linking group, and formed so that the group derived from the polyhydroxy compound is oriented toward an inner space of the hollow shell.

(iii) The polyhedral transition metal complex according to (i), the polyhedral transition metal complex being self-assembled by the transition metal atoms (M') and the bidentate organic ligands (L) including the group derived from the polyhydroxy compound via the linking group so that the group derived from the polyhydroxy compound is oriented toward the inner space of the hollow shell, the polyhedral transition metal complex being a compound shown by $M_{n1}L_{2(n1)}$ (wherein M represents a transition metal atom, and n1 is an integer from 6 to 60, provided that M may be either the same or different, and L may be either the same or different).

(iv) The polyhedral transition metal complex according to (ii), the polyhedral transition metal complex being self-assembled by the transition metal atoms (M') and the bidentate organic ligands (L) including the group derived from the polyhydroxy compound via the linking group so that the group derived from the polyhydroxy compound is oriented toward the inner space of the hollow shell, the polyhedral transition metal complex being a compound shown by $M_{n2}L_{2(n2)}$ (wherein M represents a transition metal atom, and n2 is 6, 12, 24, 30, or 60, provided that M may be either the same or different, and L may be either the same or different).

(v) The polyhedral transition metal complex according to any one of (i) to (iv), wherein the polyhydroxy compound is glucose.

(vi) The polyhedral transition metal complex according to any one of (i) to (v), wherein the transition metal atoms that form the polyhedral transition metal complex are one type of transition metal atom selected from the group consisting of Ti, Fe, Co, Ni, Cu, Zn, Ru, Rh, Pd, Cd, Os, Ir, and Pt.

(vii) The polyhedral transition metal complex according to any one of (i) to (vi), wherein the bidentate organic ligands are compounds shown by a formula (I),

[Chemical Formula 1]

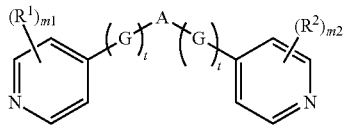
(I)

wherein $R^1$ and $R^2$ individually represent a halogen atom, a substituted or unsubstituted alkyl group, a substituted or unsubstituted alkoxy group, a cyano group, or a nitro group, m1 and m2 are individually an integer from 0 to 4, provided that a plurality of $R^1$ may be either the same or different when m1 is an integer equal to or larger than 2, and a plurality of $R^2$ may be either the same or different when m2 is an integer equal to or to larger than 2, A represents a group shown by any of formulas (a-1) to (a-4),

[Chemical Formula 2]

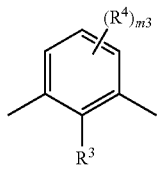
(a-1)

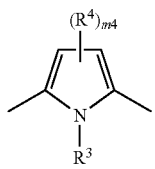
(a-2)

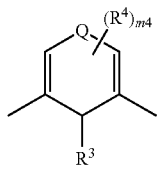
(a-3)

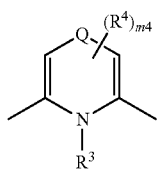
(a-4)

wherein $R^3$ represents a substituent to which a polyhydroxy compound is bonded at its end, $R^4$ represents a halogen atom, a substituted or unsubstituted alkyl group, a substituted or unsubstituted alkoxy group, a cyano group, or a nitro group, m3 is an integer from 0 to 3, m4 is an integer from 0 to 2, provided that a plurality of $R^4$ may be either the same or different when m3 is an integer equal to or larger than 2 or m4 is 2, and Q represents —Nr1- (wherein r1 represents a hydrogen atom, an alkyl group, an aryl group, or an acyl group), —O—, —C(=O)—, —S—, or —SO$_2$—.

G represents an ethynylene group or a p-phenylene group, and t is an integer from 0 to 6, provided that a plurality of G may be either the same or different when t is an integer equal to or larger than 2.

(viii) The polyhedral transition metal complex according to any one of (1) to (vi), wherein the bidentate organic ligands are compounds shown by a formula (I-1),

[Chemical Formula 3]

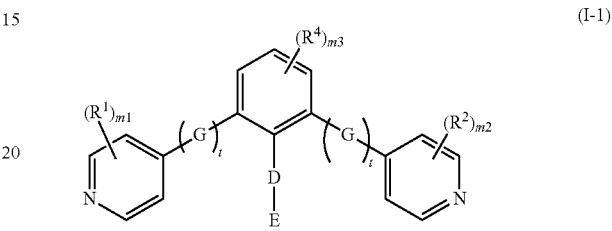
(I-1)

wherein G, t, $R^1$, $R^2$, $R^4$, m1, m2, and m3 are the same as defined above, D represents a linking group, and E represents a group derived from a polyhydroxy compound.

(ix) The polyhedral transition metal complex according to (viii), wherein the bidentate organic ligands are compounds shown by a formula (I-1a) or (I-1b),

[Chemical Formula 4]

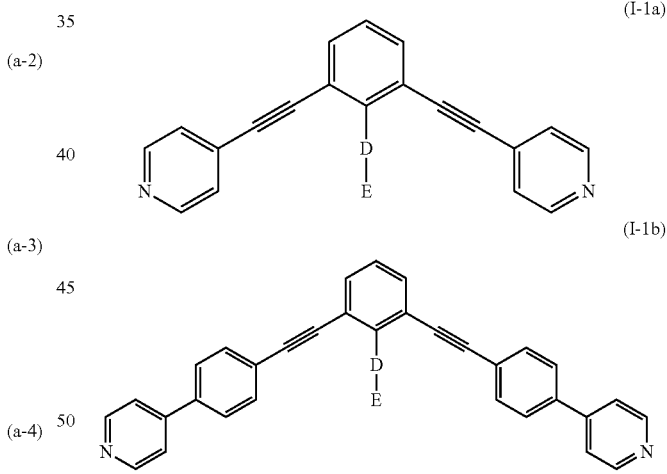
(I-1a)

(I-1b)

wherein D and E are the same as defined above.

(x) An ultrafine particle-containing transition metal complex including the polyhedral transition metal complex according to any one of (i) to (ix), and ultrafine particles of a metal oxide, the ultrafine particles being included within the hollow shell of the polyhedral transition metal complex.

(xi) The ultrafine particle-containing transition metal complex according to (x), wherein the metal oxide is silicon oxide, titanium oxide, zirconium oxide, aluminum oxide, or boron oxide.

(xii) The ultrafine particle-containing transition metal complex according to (x) or (xi), wherein the metal oxide has a (weight average molecular weight)/(number average molecular weight) ratio of 1 to 1.05.

(xiii) A method of producing the ultrafine particle-containing transition metal complex according to any one of (x) to (xii), the method including a step of adding a specific amount of a metal alkoxide to a solution of the polyhedral transition metal complex.

(xiv) The method according to (xiii), wherein the metal alkoxide is a compound shown by $(R^5)_a M^1(OR^6)_b$, wherein $M^1$ represents a silicon atom, a titanium atom, a zirconium atom, an aluminum atom, or a boron atom, $R^5$ represents an alkyl group having 1 to 6 carbon atoms, $R^6$ represents an alkyl group having 1 to 6 carbon atoms that may be substituted with an alkoxy group having 1 to 6 carbon atoms, a is 0, 1, or 2, b is 2, 3, or 4, and a value "a+b" is a valence of $M^1$.

(xv) The method according to (xiii) or (xiv), wherein the metal alkoxide is added in to an amount of 72 to 500 mol per mol of the polyhedral transition metal complex.

(xvi) The method according to any one of (xiii) to (xv), wherein a molecular weight of the ultrafine particles of the metal oxide is controlled by changing the amount of the metal alkoxide added to the solution.

Effects of the Invention

The first aspect of the invention thus provides a polyhedral transition metal complex that makes it possible to efficiently produce metal oxide particles having a uniform particle size of several nanometers within the polyhedral structure formed by a transition metal atom and a bidentate organic ligand that includes a polyhydroxy compound via a linking group.

A second aspect of the invention thus provides an ultrafine particle-containing polyhedral transition metal complex in which metal oxide particles having a uniform particle size of several nanometers are included within a polyhedral structure.

A third aspect of the invention thus makes it possible to efficiently and easily produce an ultrafine particle-containing polyhedral transition metal complex in which metal oxide particles having a uniform particle size of several nanometers are included within a polyhedral structure.

According to the third aspect of the invention, the size (molecular weight) of the metal oxide particles to be synthesized can be controlled by changing the amount of the metal alkoxide added to the solution. The size (molecular weight) of the metal oxide particles to be synthesized can also be controlled by adjusting the size of the bidentate ligand that forms the polyhedral transition metal complex.

BRIEF DESCRIPTION OF THE DRAWINGS

FIG. 9 is a view showing the $^1$H-NMR spectrum (500 MHz, 300 K, DMSO-$d_6$) after reacting a polyhedral complex (2a) with Ti(OiPr)$_4$.

DESCRIPTION OF EXEMPLARY EMBODIMENTS

Figure 1:
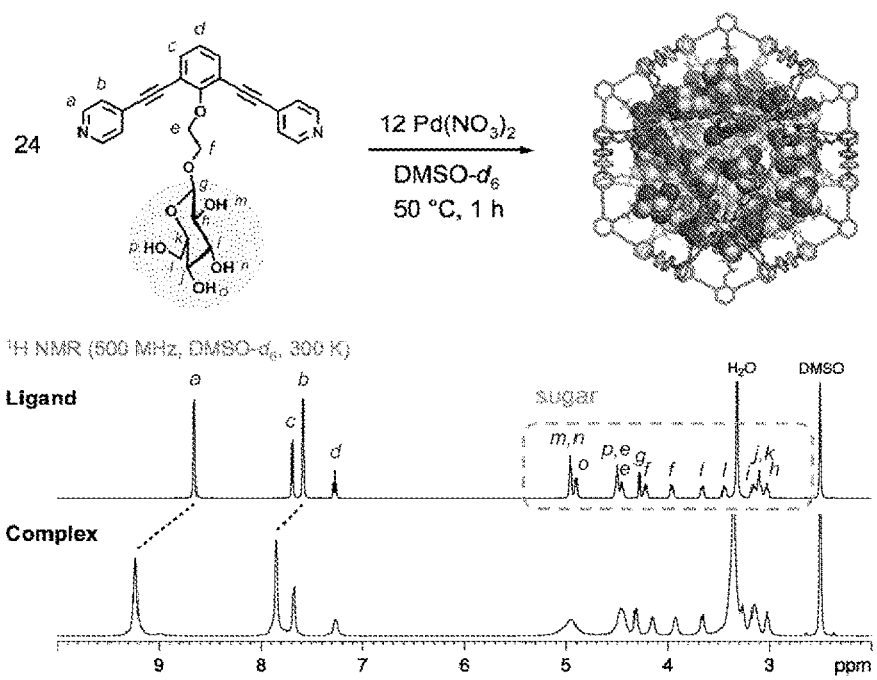
FIG. 1 is a view showing the $^1$H-NMR spectra (500 MHz, 300 K, DMSO-$d_6$) of a glucopyranoside (1) (ligand) (upper side) and a polyhedral complex (2a) (lower side).

The invention is described in detail below.

1). Polyhedral Transition Metal Complex

A polyhedral transition metal complex according to one embodiment of the invention includes a hollow shell, the hollow shell including n1 (where n1 is an integer from 6 to 60) transition metal atoms and 2(n1) bidentate organic ligands, the bidentate organic ligands including a group derived from a polyhydroxy compound via a linking group, and formed so that the group derived from the polyhydroxy compound is oriented toward the inner space of the hollow shell.

In the polyhedral transition metal complex according to one embodiment of the invention, it is preferable that n1 be n2 (where n2 is 6, 12, 24, 30, or 60), more preferably 6 or 12, and particularly preferably 12, so that self-assembly easily proceeds.

The polyhedral transition metal complex according to one embodiment of the invention is formed by self-assembly utilizing a coordinate bond between a transition metal ion and a bidentate organic ligand that includes a group derived from a polyhydroxy compound via a linking group. Since a coordinate bond has a moderate bonding force and clearly defined orientation, a molecular assembly having a precisely controlled structure can be formed spontaneously and quantitatively. Moreover, since the coordination number and the bond angle can be controlled corresponding to the type and the oxidation number of a metal, various coordination structures can be formed.

The polyhedral transition metal complex according to one embodiment of the invention is preferably self-assembled from the transition metal atoms (M') and the bidentate organic ligands (L) including the group derived from the polyhydroxy compound via the linking group so that the group derived from the polyhydroxy compound is oriented toward the inner space of the hollow shell, and shown by M (wherein M represents a transition metal atom, and n1 and L are the same as defined above), and more preferably self-assembled from the transition metal atoms (M') and the bidentate organic ligands (L) so that the linking group is oriented toward the inner space of the hollow shell, and shown by $M_{n2}L_{2n2}$ (wherein M, L, and n2 are the same as defined above). Note that M may be either the same or different, and L may be either the same or different. It is preferable that M be the same, and L be the same.

The size of the hollow shell of the polyhedral transition metal complex according to one embodiment of the invention is not particularly limited. It is preferable that the hollow shell have a diameter of 3 to 15 nm. The size of the hollow shell of the polyhedral transition metal complex depends on the size (length) of the bidentate organic ligand (L).

The transition metal atoms (M) that form the polyhedral transition metal complex according to one embodiment of the invention are not particularly limited, but are preferably one type of transition metal atom selected from the group consisting of Ti, Fe, Co, Ni, Cu, Zn, Ru, Rh, Pd, Cd, Os, Ir, and Pt, more preferably a platinum group metal such as Ru, Rh, Pd, Os, Ir, or Pt, still more preferably Ru, Pd, or Pt, and particularly preferably Pd, since a complex having a square-planar coordination can be easily formed.

The valence of the transition metal atom is normally 0 to 4, and preferably 2. The coordination number is normally 4 to 6, and preferably 4.

The bidentate organic ligands (L) that form the polyhedral transition metal complex according to one embodiment of the invention are not particularly limited as long as the bidentate organic ligands (L) include a group derived from a polyhydroxy compound at the end, and can form the polyhedral transition metal complex with the transition metal atoms in a self-assembled manner so that the group derived from the polyhydroxy compound is oriented toward the inner space of the hollow shell. It is preferable that the bidentate organic ligands be compounds shown by the following formula (I).

A compound shown by the formula (I) has two arms extending from A and having an end pyridyl group, and has a structure in which a space is formed between the pyridyl groups while maintaining planarity.

[Chemical Formula 5]

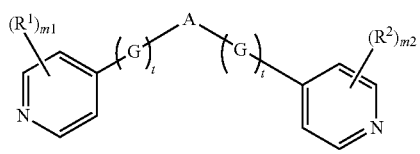

(I)

$R^1$ and $R^2$ individually represent a halogen atom, a substituted or unsubstituted alkyl group, a substituted or unsubstituted alkoxy group, a cyano group, or a nitro group.

m1 and m2 are individually an integer from 0 to 4. A plurality of $R^1$ may be either the same or different when m1 is an integer equal to or larger than 2, and a plurality of $R^2$ may be either the same or different when m2 is an integer equal to or larger than 2.

A represents a group shown by any of the following formulas (a-1) to (a-4).

[Chemical Formula 6]

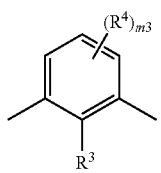

(a-1)

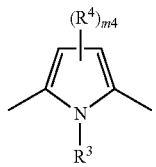

(a-2)

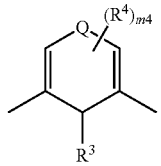

(a-3)

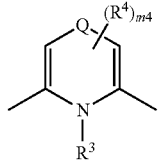

(a-4)

$R^3$ represents a substituent to which a polyhydroxy compound is bonded at its end. Specific examples of such a substituent include a group shown by -D-E (described later).

$R^4$ represents a halogen atom, a substituted or unsubstituted alkyl group, a substituted or unsubstituted alkoxy group, a cyano group, or a nitro group.

m3 is an integer from 0 to 3, and m4 is an integer from 0 to 2. A plurality of $R^4$ may be either the same or different when m3 is an integer equal to or larger than 2 or m4 is 2.

Examples of the halogen atom represented by $R^1$, $R^2$, and $R^4$ include a fluorine atom, a chlorine atom, a bromine atom, and the like.

Examples of the unsubstituted alkyl group represented by $R^1$, $R^2$, and $R^4$ include alkyl groups having 1 to 20 carbon atoms, such as a methyl group, an ethyl group, a propyl group, an isopropyl group, an n-butyl group, a t-butyl group, an n-pentyl group, an n-hexyl group, an n-acetyl group, an n-nonyl group, and an n-decyl group.

Examples of a substituent for the alkyl group represented by $R^1$, $R^2$, and $R^4$ include a halogen atom, an alkoxy group, a substituted or unsubstituted phenyl group, and the like.

Examples of the unsubstituted alkoxy group represented by $R^1$, $R^2$, and $R^4$ include alkoxy groups having 1 to 20 carbon atoms, such as a methoxy group, an ethoxy group, a propoxy group, an isopropoxy group, a butoxy group, a t-butoxy group, a pentyloxy group, and a hexyloxy group.

Examples of a substituent for the alkoxy group represented by $R^1$, $R^2$, and $R^4$ include a halogen atom, a substituted or unsubstituted phenyl group, and the like.

Q represents —Nr1- (wherein r1 represents a hydrogen atom, an alkyl group, an aryl group, or an acyl group), —O—, —C(=O)—, —S—, or —SO)—.

Examples of the alkyl group represented by r1 include a methyl group, an ethyl group, and the like. Examples of the aryl group represented by r1 include a phenyl group, a p-methylphenyl group, and the like. Examples of the acyl group represented by r1 include an acetyl group, a benzoyl group, and the like.

G represents an ethynylene group or a p-phenylene group, and t is an integer from 0 to 6. A plurality of G may be either the same or different when t is an integer equal to or larger than 2. The p-phenylene group represented by G may have a substituent at an arbitrary position.

Examples of the group represented by (G)$_t$ include, but are not limited to, the groups shown by the following formulas (b-1) to (b-8), and the like. Note that the asterisk (*) indicates the bonding position with A.

[Chemical Formula 7]

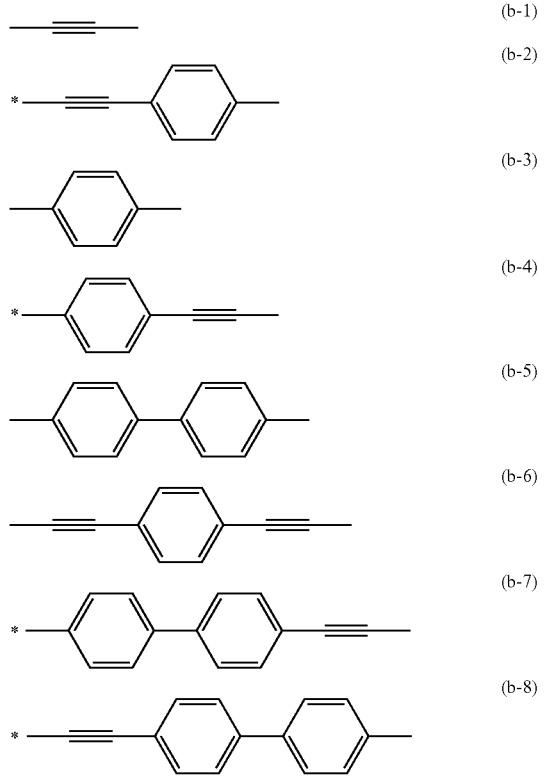

(b-1)
(b-2)
(b-3)
(b-4)
(b-5)
(b-6)
(b-7)
(b-8)

Among these, the groups shown by the formulas (b-1) and (b-2) are preferable since the polyhedral transition metal complex according to one embodiment of the invention can be easily produced.

The bidentate organic ligands (L) are more preferably compounds shown by the following formula (I-1).

[Chemical Formula 8]

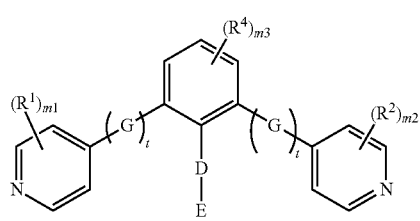

(I-1)

G, t, $R^1$, $R^2$, $R^4$, m1, m2, and m3 are the same as defined above, D represents a linking group, and E represents a group derived from a polyhydroxy compound.

Examples of the linking group represented by D include —O—, —C(=O)—, a group shown by —(CH$_2$)$_s$—, and a combination thereof. Among these, a group shown by —(CH$_2$)$_s$— is preferable from the viewpoint of availability. Note that s is an integer from 1 to 20 (preferably an integer from 1 to 10).

E represents a group derived from a polyhydroxy compound.

The term "polyhydroxy compound" used herein refers to a compound that includes two or more hydroxyl groups in the molecule. Examples of the polyhydroxy compound include glycols such as ethylene glycol, propylene glycol, and tetramethylene glycol; glycerol compounds such as diglycerol, triglycerol, and a polyglycerine that includes four or more glycerol units in the molecule; sugars such as inositol, lactose, saccharose, glucose, fructose, xylytol, mannitol, maltitol, sorbitol, and pentaerythritol; and derivatives of these compounds.

Examples of the derivatives of the above compounds include compounds obtained by substituting some or all of the hydrogen atoms included in the glycol, glycerol compound, or sugar with an alkyl group, a substituted or unsubstituted phenyl group, or an acyl group.

Among these, glucose and glucose derivatives are preferable as the polyhydroxy compound.

The group derived from the polyhydroxy compound is not particularly limited as long as the group is obtained by removing a hydrogen atom from the polyhydroxy compound and bonds to the linking group. For example, one of the hydroxyl groups (—OH) included in the polyhydroxy compound may be converted into —O—, and bond to the linking croup.

Among compounds shown by the formula (I-1), a compound in which m1, m2, and m3 are 0 is more preferable, and compounds shown by the following formula (I-1a) or (I-1b) are particularly preferable. Note that D and E are the same as defined above.

[Chemical Formula 9]

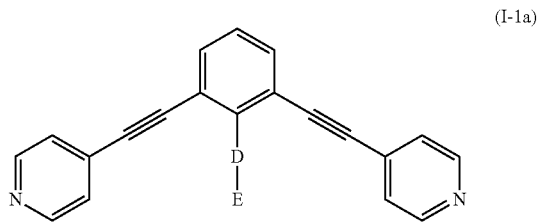

(I-1a)

(I-1b)

The bidentate organic ligand (L) may be produced by a known synthesis method.

For example, a compound shown by the following formula (I-2) may be produced as follows using the method disclosed in K. Sonogashira, Y. Tohda, N. Hagihara, Tetrahedron Lett., 1975, 4467; J. F. Nguefack, V. Bolitt, D. Sinou, Tetrahedron Lett. 1996, 31, 5527.

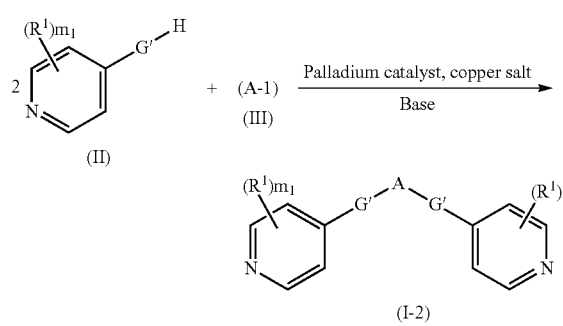

[Chemical Formula 10]

A, and R¹, and m1 are the same as defined above. G' represents a group produced when an ethynyl group (acetylene group) site bonds to A (e.g., the groups shown by the formulas (b-1), (b-2), (b-6), and (b-8)).

(A-1) represents a compound shown by X-A-X.

X represents a halogen atom (e.g., chlorine atom, bromine atom, or iodine atom).

Specifically, a compound shown by the formula (I-2) may be obtained by reacting a compound shown by the formula (II) (or a salt thereof) with a compound shown by the formula (III) in an appropriate solvent in the presence of a base, a palladium catalyst (e.g., $Pd(PhCN)_2Cl_2/P(t-Bu)$; or $Pd(PPh_3)_4$), and a copper salt (e.g., cuprous iodide).

Note that the above reaction shows an example in which two compounds shown by the formula (II) (or a salt thereof) are reacted at the same time to produce a compound that includes two identical groups. A compound that includes different groups may be obtained by reacting compounds shown by the formula (II) (or a salt thereof) stepwise under the same reaction conditions.

Examples of the base include amines such as dimethylamine, diethylamine, diisopropylamine, triethylamine, and diisopropylethylamine.

Examples of the solvent include ethers such as 1,4-dioxane, diisopropyl ether, tetrahydrofuran (THF), and 1,3-dimethoxyethane; amides such as dimethylformamide; sulfoxides such as dimethylsulfoxide; nitriles such as acetonitrile; and the like.

The reaction temperature is normally 0° C. to the boiling point of the solvent, and preferably 10 to 70° C. The reaction time is normally several minutes to several tens of hours. The reaction time is adjusted depending on the reaction scale and the like.

A compound shown by the formula (I) in which G' represents a single bond or directly links the phenyl group to A (e.g., the groups shown by the formulas (b-3), (b-4), (b-5), and (b-7)) may be produced by a known method (e.g., Suzuki-Miyaura coupling reaction or Stifle cross-coupling reaction (see below)).

Book that Outlines the Above Coupling Reaction

"Metal-Catalyzed Cross-Coupling Reactions", Armin de Meijere, Franois Diederich, Wiley-VCH Paper that Outlines the Above Coupling Reaction "Palladium-Catalyzed Cross-Coupling Reactions in Total Synthesis", K. C. Nicolaou, Paul G. Bulger, David Sarlah, Angew. Chem. Int. Ed., 2005, 44, 4442-4489

Paper that Outlines Ligand Synthesis Using the Above Coupling Reaction

"Fluorous Nanodroplets Structurally Confined in an Organopalladium Sphere", S. Sato, J. Iida, K. Suzuki, M. Kawano, T. Ozeki, and M. Fujita, Science., 2006, 313, 1273-1276

"24-Fold Endohedral Functionalization of a Self-assembled M12L24 Coordination Nanoball", M. Tominaga, K. Suzuki, T. Murase, and M. Fujita, J. Am. Chem. Soc., 2005, 127, 11950-11.951

A compound shown by the formula (II) (or a salt thereof) may be produced by a known method. Note that a commercially available product may be used as a compound shown by the formula (II) (or a salt thereof).

A compound shown by the formula (III) may be synthesized by the following method, for example.

[Chemical Formula 11]

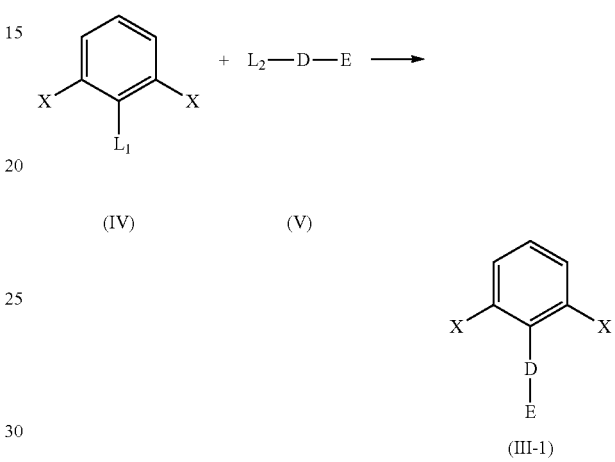

D, E, and X are the same as defined above. $L_1$ and $L_2$ represent a leaving group shown in Table 1. Examples of a combination of $L_1$ and $L_2$ are given below. In Table 1, —$Y_1$-D'- represents -D-. R represents a hydrocarbon group such as a methyl group, an ethyl group, or a phenyl group.

TABLE 1

| —$Y_1$—D'— | $L_1$ | $L_2$ |
|---|---|---|
| —O—D'— | OH | Halogen atom, OH, or $OSO_2R$ |
| —C(=O)—O—D'— | COOH or COCl | OH |
| —C(=O)—D'— | COCl | Active hydrogen atom |
| —O—C(=O)—D'— | OH | COOH or COCl |

A compound shown by the formula (IV) and a compound shown by the formula (V) may be reacted by a known method that forms various chemical bonds (e.g., —O—, —C(=O)—O—, —C(=O)—, or —O—C(=O)—) (refer to Sandler and Karo, Organic Functional Group Preparations [I] and [II], Hirokawa Publishing, 1976, for example).

For example, a compound shown by the formula (III-1) in which $Y_1$ is an oxygen atom may be obtained by reacting a compound shown by the formula (IV) in which $L_1$ is OH with a compound shown by the Formula (V) in which $L_2$ is a halogen atom in the presence of a base.

Examples of the base include inorganic bases such as sodium hydrogen carbonate, sodium carbonate, potassium carbonate, sodium hydroxide, and sodium hydride; amines such as triethylamine, pyridine, and 1,8-diazabicyclo[5.4.0]-7-undecene (DBU); metal alkoxides such as potassium t-butoxide and sodium methoxide; and the like.

The above reaction is preferably carried out in a solvent. The solvent is not particularly limited as long as the solvent is inert to the reaction. Examples of the solvent include ethers such as diethyl ether, THF, and 1,4-dioxane; aromatic hydrocarbons such as benzene, toluene, and xylene; halogenated hydrocarbons such as dichloromethane, chloroform, and ethylene dichloride; nitriles such as acetonitrile; amides such as dimethylformamide (DMF); sulfoxides such as dimethyl sulfoxide (DMSO); aromatic amines such as pyridine; and the like.

The above reaction proceeds smoothly in a temperature range from −15° C. to the boiling point of the solvent. The reaction time differs depending on the reaction scale and the like, but is normally several minutes to 50 hours.

Many of the compounds shown by the formula (V) are known substances, and may be produced by a known method.

The transition metal compound (M') is not particularly limited as long as the transition metal compound (M') forms the polyhedral transition metal complex with the bidentate organic ligand (L) in a self-assembled manner. The transition metal compound (M') is particularly preferably a divalent transition metal compound.

Specific examples of the transition metal compound (M') include halides, nitrates, hydrochlorides, sulfates, acetates, methanesulfonates, trifluoromethanesulfonate, p-toluenesulfonates, tetrafluoroborates ($BF_4$), and the like of a transition metal. The transition metal compound (M') may include a neutral ligand such as ethylenediamine, acetonitrile, or triphenylphosphine. Among these, a nitrate or a trifluoromethanesulfonate of a transition metal is preferable since the target polyhedral transition metal complex can be efficiently obtained.

The transition metal compounds (M') and the bidentate organic ligands (L) may be used in an appropriate ratio depending on the composition of the target polyhedral transition metal complex and the like. For example, when producing a transition metal complex having a composition shown by $M_{12}L_{24}$, 2 to 3 mol of the bidentate organic ligands (L) may be reacted with 1 mol of the transition metal compounds (M').

The transition metal compounds (M') and the bidentate organic ligands (L) may be reacted in an appropriate solvent. Examples of the solvent include nitriles such as acetonitrile; sulfoxides such as dimethyl sulfoxide (DMSO); amides such as N,N-dimethylformamide; ethers such as diethyl ether, tetrahydrofuran, 1,2-dimethoxyethane, and 1,4-dioxane; halogenated hydrocarbons such as dichloromethane and chloroform; aliphatic hydrocarbons such as pentane and hexane; aromatic hydrocarbons such as benzene and toluene; alcohols such as methanol, ethanol, and isopropyl alcohol; ketones such as acetone and methyl ethyl ketone; cellosolves such as ethylcellosolve; water; and the like. These solvents may be used either individually or in combination.

The reaction between the transition metal compounds (M') and the bidentate organic ligands (L) proceeds smoothly in a temperature range from 0° C. to the boiling point of the solvent.

The reaction time is several minutes to several days.

After completion of the reaction, the resulting product is subjected to a normal post-treatment (e.g., filtration, column purification using an ion-exchange resin or the like, distillation, and recrystallization) to isolate the target polyhedral transition metal complex.

A polyhedral transition metal complex may be obtained using a compound shown by the formula (I) in which the hydroxyl groups of the polyhydroxy compound are protected with a protecting group (e.g., acetyl group or benzoyl group), and the hydroxyl groups may be deprotected by a known method to obtain the target polyhedral transition metal complex.

The counter ion of the resulting polyhedral transition metal complex is normally the anion of the transition metal compound (M'). The counter ion may be exchanged with another counter ion in order to improve the crystallinity or the stability of the polyhedral transition metal complex. Examples of the counter ion include $PF_6^-$, $ClO_4^-$, $SbF_4^-$, $AsF_6^-$, $BF_4^-$, $SiF_6^{2-}$, and the like.

2) Ultrafine Particle-Containing Transition Metal Complex

An ultrafine particle-containing transition metal complex according to one embodiment of the invention includes the polyhedral transition metal complex according to one embodiment of the invention, and ultrafine particles of a metal oxide, the ultrafine particles being included within the hollow shell of the polyhedral transition metal complex.

The metal oxide included within the hollow shell of the polyhedral transition metal complex is not particularly limited. Examples of the metal oxide include silicon oxide, titanium oxide, zirconium oxide, aluminum oxide, boron oxide, germanium oxide, barium oxide, calcium oxide, indium oxide, lanthanum oxide, yttrium oxide, niobium oxide, tungsten oxide, and the like. Among these, silicon oxide, titanium oxide, zirconium oxide, aluminum oxide, and boron oxide are preferable, and silicon oxide and titanium oxide are particularly preferable.

The molecular weight of the metal oxide differs depending on the size of the hollow space of the polyhedral transition metal complex, but is normally 1000 to 35,000 Da.

The molecular weight distribution ((weight average molecular weight)/(number average molecular weight)) of the metal oxide is normally 1 to 1.1, preferably 1 to 1.05, and still more preferably 1.005 to 1.01.

3) Method of Producing Ultrafine Particle-Containing Polyhedral Transition Metal Complex A method of producing an ultrafine particle-containing transition metal complex according to one embodiment of the invention includes adding a specific amount of a metal alkoxide to a solution of the polyhedral transition metal complex according to one embodiment of the invention.

The method according to one embodiment of the invention utilizes a phenomenon in which a polyhydroxy compound such as a sugar functions as a reaction catalyst during hydrolysis and polycondensation of a metal alkoxide (see Non-patent Documents 2 and 3).

Specifically, when adding a specific amount of a metal alkoxide to a solution of the polyhedral transition metal complex according to one embodiment of the invention, the metal alkoxide is drawn toward the group derived from the polyhydroxy compound present in the inner space of the polyhedral transition metal complex, enters the inner space of the polyhedral transition metal complex, and undergoes hydrolysis and polycondensation to produce a particulate metal oxide.

The solvent is not particularly limited as long as the solvent dissolves the polyhedral transition metal complex according to one embodiment of the invention and the metal alkoxide. Examples of the solvent include sulfur-containing solvents such as dimethyl sulfoxide, diethyl sulfoxide, sulfolane, and carbon disulfide; amide solvents such as N,N-dimethylformamide, N,N-dimethylacetamide, N-methylpyrrolidone, and hexamethylphosphoric triamide; ether solvents such as tetrahydrofuran, 1,2-dimethoxyethane, and 1,4-dioxane; halogenated hydrocarbons such as dichloromethane, chloroform, and carbon tetrachloride; nitrite solvents such as acetonitrile; a mixed solvent of two or more of these solvents; and the like.

The metal alkoxide is not particularly limited. Examples of the metal oxide include silicon alkoxides, titanium alkoxides, zirconium alkoxides, aluminum alkoxides, boron alkoxides, germanium alkoxides, barium alkoxides, calcium alkoxides, indium alkoxides, lanthanum alkoxides, yttrium alkoxides, niobium alkoxides, tungsten alkoxides, and the like.

Among these, it is preferable that the metal alkoxide be a compound shown by the formula (VI): $(R^5)_aM(OR^6)_b$.

M in the formula (VI) represents a silicon atom, a titanium atom, a zirconium atom, an aluminum atom, or a boron atom, and preferably represents a silicon atom or a titanium atom.

$R^5$ represents an alkyl group having 1 to 6 carbon atoms, such as a methyl group, an ethyl group, or an n-propyl group.

$R^6$ represents an alkyl group having 1 to 6 carbon atoms (e.g., methyl group, ethyl group, n-propyl group, n-butyl group, or 2-hydroxyethyl group) that May be substituted with an alkoxy group having 1 to 6 carbon atoms.

a is 0, 1, or 2, b is 2, 3, or 4, and the value "a+b" is the valence of M.

Specific examples of compounds shown by the formula (VI) include slime alkoxides such as tetramethoxysilane, tetraethoxysilane, tetrapropoxysilane, tetraisopropoxysilane, tetrabutoxysilane, tetrakis(2-hydroxyethoxy)silane, methyl trimethoxysilane, and methyltriethoxysilane; titanium alkoxides such as tetramethoxytitanium, tetraethoxytitanium, tetrapropoxytitanium, tetraisopropoxytitanium, and tetrabutoxytitanium; zirconium alkoxides such as tetramethoxyzirconium, tetraethoxyzirconium, tetrapropoxyzirconium, tetraisopropoxyzirconium, and tetrabutoxyzirconium; aluminum alkoxides such as trimethoxyaluminum, triethoxyaluminum, tripropoxyaluminum, triisopropoxyaluminum, and tributoxyaluminum; boron alkoxides such as trimethoxyborane, triethoxyborane, tripropoxyborane, tri-isopropoxyborane, and tributoxyborane; and the like.

The metal alkoxide is normally added in an amount of 20 to 700 mol (preferably 72 to 500 mol) per mol of the polyhedral transition metal complex.

A proton acid may be added to the reaction system. The polycondensation reaction of the metal alkoxide may be promoted by adding a proton acid. Examples of the proton acid include nitric acid, sulfuric acid, hydrochloric acid, acetic acid, and the like. The proton acid is normally added in an amount of 0.01 to 1.0 mol per mol of the polyhedral transition metal complex.

In the method of producing an ultrafine particle-containing transition metal complex according to one embodiment of the invention, the molecular weight (size) of the ultrafine particles of the metal oxide may be controlled by changing the amount of the metal alkoxide added to the solution.

In general, metal oxide particles having a higher molecular weight and a larger particle size can be obtained by increasing the amount of the metal alkoxide added to the solution. However, since the reaction by which the metal oxide is produced from the metal alkoxide proceeds within the hollow space of the polyhedral transition metal complex, the size of the metal oxide particle does not exceed the size of the hollow space of the polyhedral transition metal complex.

For example, when using a polyhedral transition metal complex formed by 2-[2,6-bis(4-pyridylethynyl)phenoxy] ethyl D-glucopyranoside and Pd(NO$_3$)$_2$, and using tetramethoxysilane (TMOS) as the metal alkoxide, silica nanoparticles having an Mw of 5270 are obtained when using TMOS in an amount of 65 equivalents based on the polyhedral complex. Silica nanoparticles having an Mw of 6650 are obtained when using TMOS in an amount of 85 equivalents, silica nanoparticles having an Mw of 9390 are obtained when using TMOS in an amount of 130 equivalents, and silica nanoparticles having an Mw of 11,100 are obtained when using TMOS in an amount of 170 equivalents.

The molecular weight (size) of the metal oxide particles to be synthesized can also be controlled by adjusting the size of the polyhedral transition metal complex.

For example, when using 2-[2,6-bis(4-pyridylethynyl)phenoxy]ethyl β-D-glucopyranoside as the bidentate organic ligand that forms the polyhedral transition metal complex, since the size of the inner space of the resulting complex increases as compared with the case of using 2-[2,6-bis(4-pyridylethynyl)phenoxy]ethyl D-glucopyranoside, silica nanoparticles having an Mw of 31,690 can be obtained when using TMOS in an amount of 500 equivalents based on the polyhedral complex.

The structure of the resulting ultrafine particle-containing transition metal complex may be confirmed by a known analysis means (e.g., $^1$H-NMR, $^{13}$C-NMR, IR to spectrum, mass spectrum, visible absorption spectrum, UV absorption spectrum, reflection spectrum, X-ray crystal structure analysis, or elemental analysis).

The ultrafine particle-containing transition metal complex according to one embodiment of the invention can thus be efficiently produced by a simple operation. Therefore, the ultrafine particle-containing transition metal complex can be mass-produced (e.g., several grams).

EXAMPLES

The invention is further described below by way of examples. Note that the invention is not limited to the following examples.

Instruments (1) Measurement of $^1$H-NMR Spectrum and $^{13}$C-NMR Spectrum

The $^1$H-NMR spectrum and the $^{13}$C-NMR spectrum were measured using a Bruker DRX 500 NMR spectrometer, a Bruker AV-500 NMR spectrometer, and a JEOL JNM-AL 300 NMR spectrometer.

TMS was used as the internal standard. The chemical shift was indicated by the δ value. The meanings of the abbreviations are s (singlet), d (doublet), t (triplet), and br (broad).

(2) Measurement of Mass Spectrum

Cold-spray ionization mass spectrometry (CSI-MS) was performed using a JEOL JMS-700C mass spectrometer.

(3) Mass Spectrometry

Laser desorption/ionization mass spectrometry (LDI-MS) was performed using an Applied Biosystem Voyager DE-STR mass spectrometer.

(4) The melting point was measured using a Yanaco MP-500V micro melting point measuring system.

(5) An elemental analysis was performed using a Yanaco MT-6 elemental analyzer.

(6) The MALDI-TOFMS spectrum was measured using a TOF mass spectrometer (Applied Biosystem Voyager DE-STR).

(7) An AFM image was obtained using a JEOL JSPM-5200 scanning probe microscope.

(8) LDI-MS

Laser desorption/ionization mass spectrometry (LDI-MS) was performed using an Applied Biosystem Voyager DE-STR mass spectrometer.

(9) TEM observation (electron microscopy) was performed using a JEOL JEM-2010HC electron microscope.

(10) The $^{29}$Si-MAS-NMR spectrum (solid-state NMR) was measured using a Chemagnetics CMX-300 spectrometer.

(11) An X-ray fluorescence (XRF) analysis was performed using a JEOL JSX-3400RII XRF) analyzer.

(12) Energy-dispersive X-ray spectroscopy (EDS) was performed using a JEOL JEM-2010HC transmission electron microscope.

Reagents

Organic synthesis dehydrated solvents (water content: 0.005% or less) commercially available from TCI, Wako Pure Chemical Industries, Ltd., and Sigma-Aldrich were used as the reaction solvents.

Commercially available reagents were directly used without further purification.

Example 1

Synthesis of $M_{12}L_{24}$ Polyhedral Transition Metal Complex (Polyhedral Complex (2a))

(1) Synthesis of 2-[2,6-bis(4-pyridylethynyl)phenoxy]ethyl D-glucopyranoside (1)

[Chemical Formula 12]

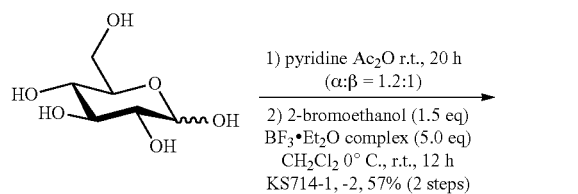

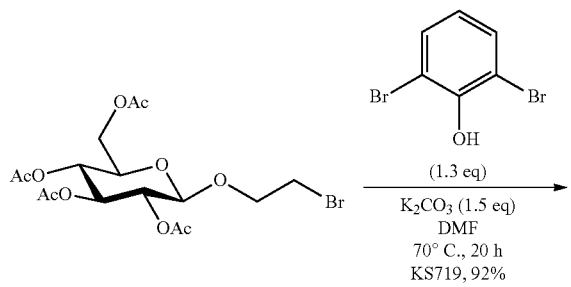

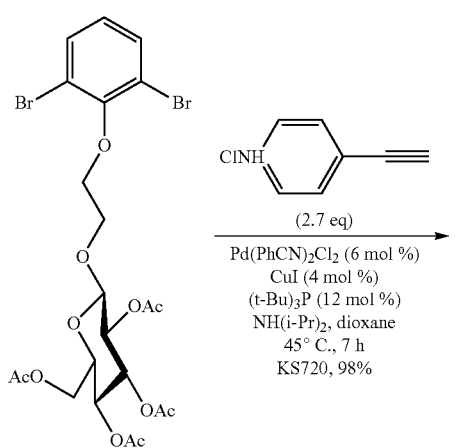

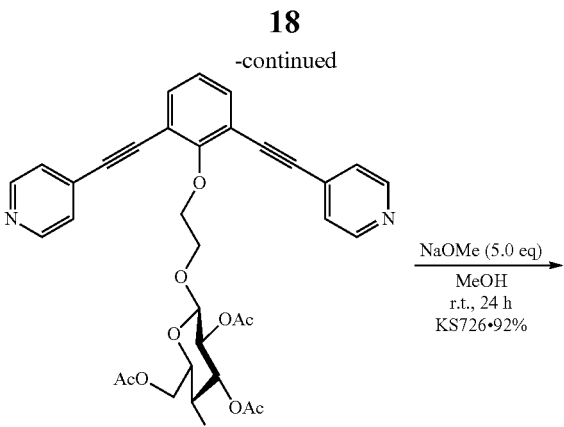

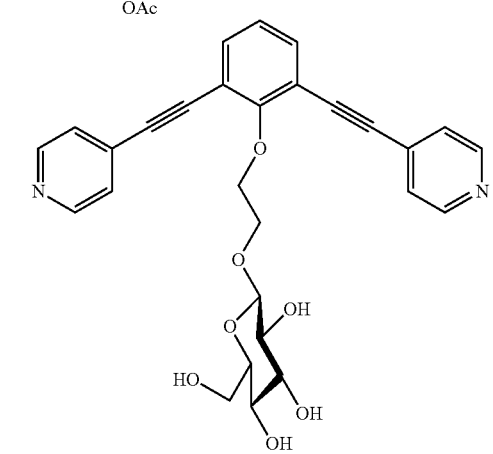

(i) Synthesis of 2-(2,6-dibromophenoxy)ethyl 2,3,4,6-tetra-O-acetyl-D-glucopyranoside 2,6-Dibromophenol (688 mg, 2.73 mmol), potassium carbonate (435 mg, 2.73 mmol), and 2-bromoethyl 2,3,4,6-tetra-O-acetyl-glucopyranoside (934 mg, 2.05 mmol) were stirred in N,N-dimethylformamide (8 ml) at 70° C. for 20 hours in an argon atmosphere.

The reaction mixture was diluted with ethyl acetate (100 ml), washed three times with water (100 ml), dried over anhydrous sodium sulfate, and concentrated under reduced pressure. The residue was purified by silica gel column chromatography (eluant: n-hexane:chloroform=2:1 to 1:2 (volume ratio)) to obtain the target product as white crystals (1.18 g, yield: 92%).

The NMR data of the product is given below.

$^1$H-NMR (500 MHz, CDCl$_3$, 27° C., δ ppm) 7.50 (d, J=8.0 Hz, 2H), 6.87 (t, J=8.0 Hz, 1H), 5.23 (t, J=9.4 Hz, 1H), 5.11 (t, J=9.8 Hz, 1H), 5.06 (t, J=9.2 Hz, 1H), 4.75 (d, J=7.4 Hz, 1H), 4.30-4.23 (m, 2H), 4.21-4.16 (m, 2H), 4.15-4.09 (m, 1H), 4.09-4.04 (m, 1H), 3.78-3.72 (m, 1H), 2.08 (s, 3H), 2.06 (s, 3H), 2.03 (s, 3H), 2.01 (s, 3H)

$^{13}$C-NMR (125 MHz, CDCl$_3$, 27° C., δ ppm) 170.7 (C), 170.3 (C), 169.5 (C), 169.4 (C), 153.1 (C), 132.8 (CH), 126.5 (CH), 118.4 (C), 100.8 (C), 72.9 (CH), 72.0 (CH$_2$), 71.9 (CH), 71.3 (CH), 68.5 (CH), 68.4 (CH$_2$), 62.0 (CH$_2$), 20.84 (C), 20.75 (C), 20.63 (C), 20.61 (C)

Elemental analysis: Calcd for $C_{22}H_{26}Br_2O_{11}$: C, 42.19; H, 4.18.

Found: C, 41.92; H, 4.01.

(ii) Synthesis of 2-[2,6-bis(4-pyridylethynyl)phenoxy]ethyl 2,3,4,6-tetra-O-acetyl-D-glucopyranoside Tri-t-butylphosphine (0.449 ml:0.180 mmol, 10% n-hexane solution) and diisopropylamine (1.5 ml, 10.7 mmol) were added to a 1,4-dioxane (5.0 ml) solution of 2-(2,6-dibromophenoxy)ethyl 2,3,4,6-tetra-O-acetyl-D-glucopyranoside (939 mg, 1.50 mmol), 4-ethynylpyridine hydrochloride (565 mg, 4.05 mmol), Pd(PhCN)$_2$Cl$_2$ (34.5 mg, 0.090 mmol), and cuprous iodide (11.4 mg, 0.060 mmol) in an argon atmosphere, and the mixture was stirred at 45° C. for 7 hours.

The reaction mixture was diluted with ethyl acetate (30 ml), washed twice with water (50 ml), washed with a 5% ethylenediamine aqueous solution (40 ml), washed twice with water (50 ml), and washed with saturated saline (50 ml). The organic layer was dried over anhydrous sodium sulfate, and concentrated under reduced pressure. The residue was purified by silica gel column chromatography (eluant: chloroform:methanol=30:1 (volume ratio)) to obtain the target product as white crystals (990 mg, yield: 98%).

The NMR data of the product is given below.

$^1$H-NMR (500 MHz, CDCl$_2$, 27° C. δ ppm) 8.66 (d, J=6.2 Hz, 4H), 7.54 (d, J=8.0 Hz, 2H), 7.42 (d, J=6.2 Hz, 4H), 7.12 (t, j=7.8 Hz, 1H), 5.16 (t, j=9.5 Hz, 1H), 5.04 (t, j=9.4 Hz, 1H), 4.97 (t, j=8.0 Hz, 1H), 4.65 (t, j=8.0 Hz, 1H), 4.62-4.57 (m, 1H), 4.47-4.43 (m, 1H), 4.24-4.18 (m, 2H), 4.09-4.02 (m, 2H), 3.61-3.57 (m, 1H), 2.02 (s, 3H), 2.0.1 (s, 3H), 1.99 (s, 3H), 1.92 (s, 3H).

$^{13}$C-NMR (125 MHz, CDCl$_3$. 27° C., δ ppm) 170.5 (C), 170.2 (C), 169.4 (C), 169.3 (C), 161.4 (C), 150.0 (CH), 134.8 (CH), 131.1 (C), 125.4 (CH), 123.8 (CH), 116.4 (C), 101.2 (CH), 91.5 (C), 89.5 (C), 73.1 (CH$_2$), 72.7 (CH), 72.0 (CH), 71.2 (CH), 69.2 (CH$_2$), 68.3 (CH), 61.9 (CH$_2$), 20.66 (C), 20.59 (C), 20.57 (C), 20.55 (C).

Elemental analysis: Calcd for C$_{36}$H$_{34}$N$_2$O$_{11}$: C, 64.47; H, 5.11; N, 4.18.
Found: C, 64.28; H, 5.12; N, 4.18.

(iii) Synthesis of 2-[2,6-bis(4-pyridylethynyl)phenoxy]ethyl D-glucopyranoside (1)

2-[2,6-Bis(4-pyridylethynyl)phenoxy]ethyl 2,3,4,6-tetra-O-acetyl-D-glucopyranoside (600 mg, 0.895 mmol) and a methanol (90 ml) solution of sodium methoxide (242 mg, 4.47 mmol) were stirred at room temperature for 12 hours. The reaction mixture was neutralized with a sodium hydrogen carbonate aqueous solution, and concentrated under reduced pressure. The residue was washed with water, and dried to obtain 391 mg of the target product as a white solid (yield: 87%).

The NMR data and the elemental analysis results for the product are given below.

$^1$H-NMR (500 MHz, DMSO-d$_6$, 27° C., δ ppm) 8.66 (d, j=5.5 Hz, 4H), 7.69 (d, j=7.8 Hz, 2H), 7.59 (d, j=5.6 Hz, 4H), 7.27 (t, j=8.0 Hz, 1H), 4.99-4.93 (m, 2H), 4.92-4.88 (m, 1H), 4.53-4.49 (m, 2H), 4.49-4.43 (m, 1H), 4.28 (d, j=7.6 Hz, 1H), 4.26-4.20 (m, 1H), 3.99-3.94 (m, 1H), 3.69-3.64 (m, 1H), 3.47-3.42 (m, 1H), 3.18-3.13 (m, 1H), 3.13-3.06 (m, 2H), 3.05-3.01 (m, 1H)

$^{13}$C-NMR (125 MHz, CDCl$_3$, 27° C., δ ppm) 157.8 (C), 149.9 (CH), 134.0 (CH), 130.8 (C), 125.5 (CH), 120.7 (CH), 109.6 (C), 92.7 (C), 88.1 (C)

Elemental analysis: Calcd for C$_{28}$H$_{26}$N$_2$O$_7$H$_2$O: C, 64.61; H, 5.42; N, 5.38.
Found: C, 64.34; H, 5.50; N, 5.31.

(2) Synthesis of M$_{12}$L$_{24}$ Polyhedral Transition Metal Complex (Polyhedral Complex (2a))

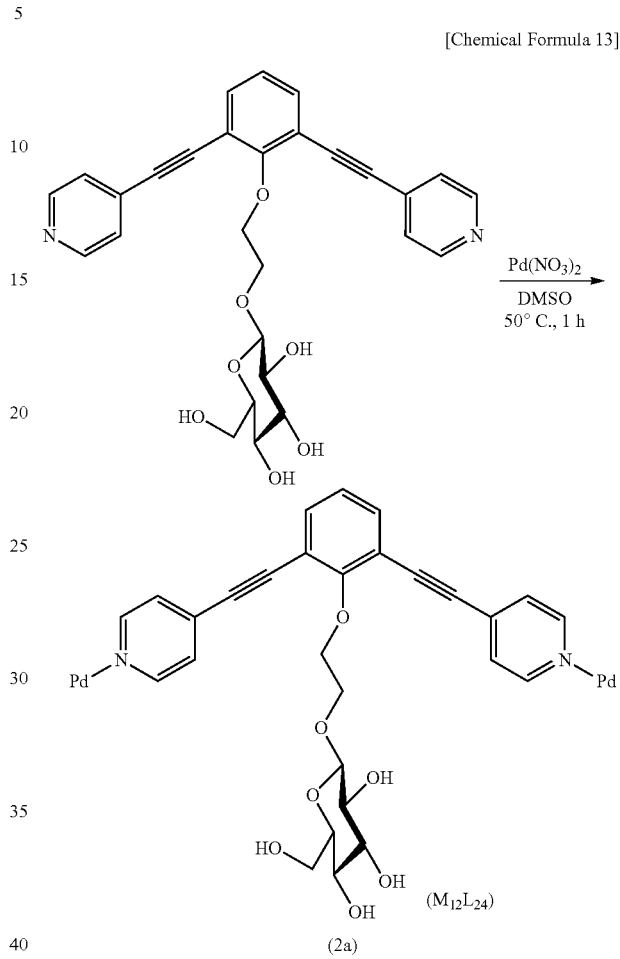

[Chemical Formula 13]

(2a)

The glucopyranoside (1) (105 mg, 0.20 mmol) obtained in (1) was added to a dimethyl sulfoxide (DMSO) solution of Pd(NO$_3$)$_2$ (10 mM, 10 ml), and the mixture was stirred at 50° C. for 1 hour.

It was confirmed by $^1$H-NMR analysis that the polyhedral complex (2a) was obtained quantitatively.

A white solid precipitated when adding ethyl acetate and diethyl ether to the reaction mixture. The white solid was collected by filtration, washed with diethyl ether, and dried under vacuum to obtain the target polyhedral complex (2a) (yield: 85%). FIG. 1 shows the structure of the polyhedral complex (2a).

The NMR data and the mass spectrometry results for the polyhedral complex (2a) are given below.

$^1$H-NMR (500 MHz, DMSO-d$_6$, 27° C., δ ppm) 9.24 (br, 96H), 7.85 (br, 96H), 7.68 (br, 48H), 7.27 (br, 24H), 4.97 (br, 72H), 4.46 (br, 72H), 4.32 (br, 24H), 4.15 (br, 24H), 3.93 (br, 24H), 3.66 (br, 24H), 3.25 (br, 24H), 3.1.5 (br, 48H), 3.02 (br, 24H).

$^{13}$C-NMR (125 MHz, DMSO-d$_6$, 27° C., δ ppm) 162.2 (C), 151.0 (CH), 136.0 (CH), 134.2 (C), 128.5 (CH), 124.5 (CH); 11.5.1 (C), 102.9 (CH), 93.8 (C), 89.9 (C), 76.7 (CH), 76.7 (CH), 74.2 (CH$_2$), 73.3 (CH), 70.1 (CH), 67.9 (CH$_2$), 61.1 (CH$_2$).

CSI-MS (NO$_3^-$ salt, DMSO:CHCl$_3$:CH$_3$CN=1:50:15): m/z 2056.3 [M-7(NO$_3^-$)]$^{7+}$, 1791.5 [M-8(NO$_3^-$)]$^{8+}$, 1585.5 [M-9(NO$_3^-$)]$^{9+}$, 1420.9 [M-10(NO$_3^-$)]$^{10+}$, 1286.1 [M-11(NO$_3^-$)]$^{11+}$, 1173.7 [M-12(NO$_3^-$)]$^{12+}$, 1078.7 [M-13(NO$_3^-$)]$^{13+}$.

FIG. 1 shows the $^1$H-NMR spectra (500 MHz, 300 K, DMSO-d$_6$) of the glucopyranoside (1) (ligand) (upper side) and the polyhedral complex (2a) (lower side).

Example 2

Synthesis of Silica Nanoparticle-Containing Complex

A DMSO solution (10 ml) of the polyhedral complex (2a) obtained in Example 1 was diluted with chloroform (90 ml). After the addition of tetramethoxysilane (TMOS) (96 equivalents based on the polyhedral complex (2a)), the mixture was condensed at room temperature for 10 days.

Figure 2:
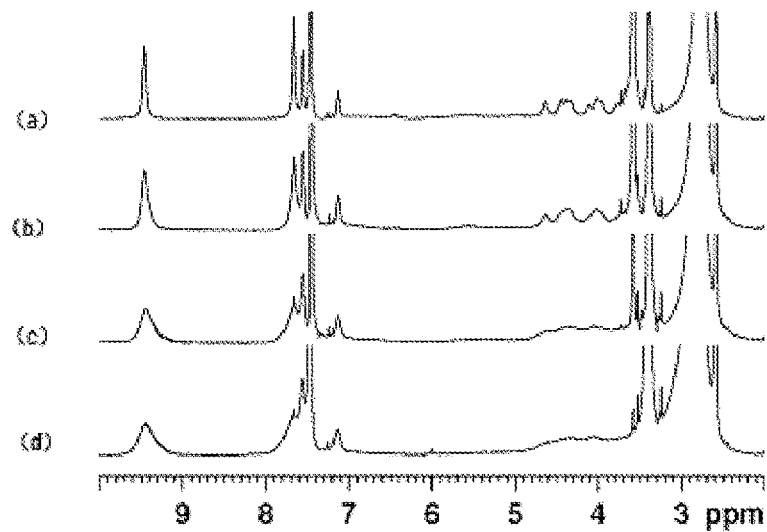
FIG. 2 is a view showing a change in $^1$H-NMR spectrum (500 MHz, 300 K, DMSO-$d_6$:CDCl$_3$=1:9) when adding TEMOS in an amount of 96 equivalents based on a polyhedral complex (2a).

The reaction was tracked by $^1$H-NMR analysis. As shown in FIG. 2, a signal attributed to the polyhedral complex became significantly broad when TMOS was hydrolyzed, and a signal attributed to methanol appeared. This suggests that silica nanoparticles were produced within the polyhedral complex. In FIG. 2, (a) indicates the $^1$H-NMR spectrum when 30 minutes had elapsed after the addition of TEMOS, (b) indicates the $^1$H-NMR spectrum when 4 hours had elapsed after the addition of TEMOS, (c) indicates the $^1$H-NMR spectrum when 24 hours had elapsed after the addition of TEMOS, and (d) indicates the $^1$H-NMR spectrum when 96 hours had elapsed after the addition of TEMOS.

Figure 3:
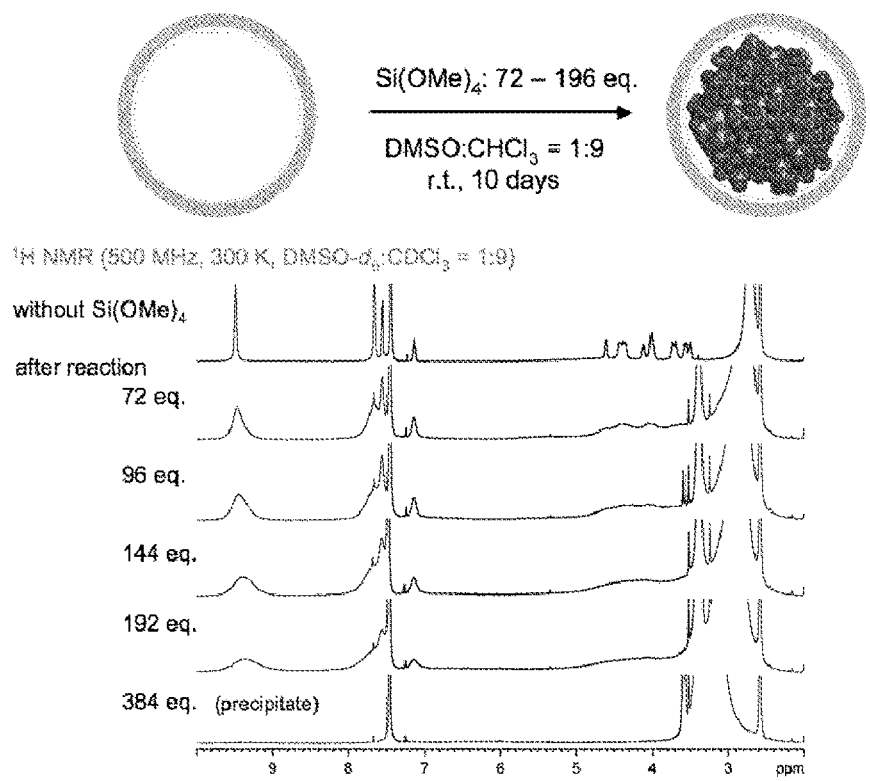
FIG. 3 is a view showing the $^1$H-NMR spectrum (500 MHz, 300 K, DMSO-$d_6$:CDCl$_3$=1:9) when 10 days had elapsed after adding TMOS in an amount of 72, 96, 144, 192, or 384 equivalents based on a polyhedral complex (2a).

A similar $^1$H-NMR spectrum was obtained when changing the amount of TMOS to 72, 144, or 192 equivalents based on the polyhedral complex (2a). As shown in FIG. 3, a signal attributed to the polyhedral complex became broader along with an increase in the amount of TMOS.

Figure 4:
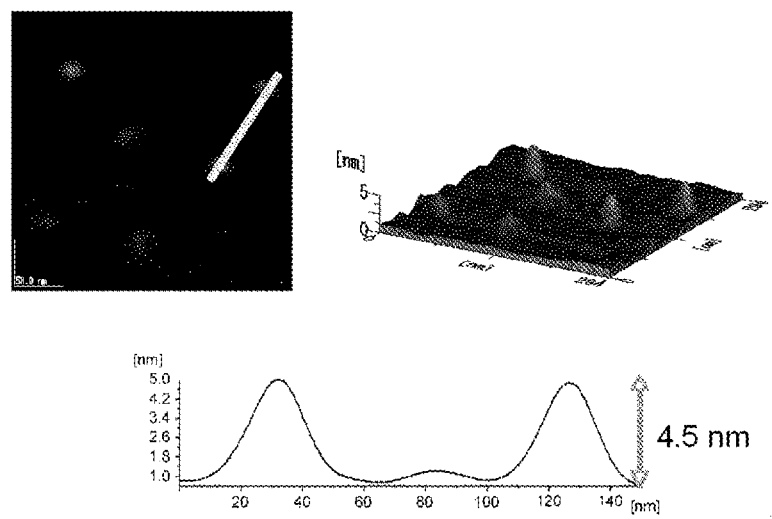
FIG. 4 is a view showing an atomic force microscope image of a silica nanoparticle-containing polyhedral complex obtained by adding TMOS in an amount of 96 equivalents based on a polyhedral complex (2a).

As shown in FIG. 4, uniform particles having a diameter of 4.5 nm (corresponding to the size of the polyhedral complex) were observed by atomic force microscopy (AFM). It was thus confirmed that the silica particles were produced in the inner space of the polyhedral complex.

Figure 5:
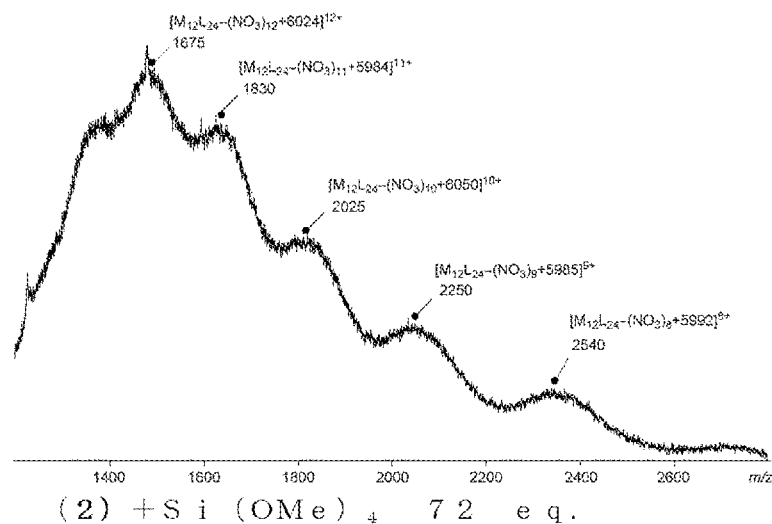
FIG. 5 is a view showing the CSI-MS spectrum of a silica nanoparticle-containing polyhedral complex obtained by adding TMOS in an amount of 72 equivalents based on a polyhedral complex (2a).
Figure 6:
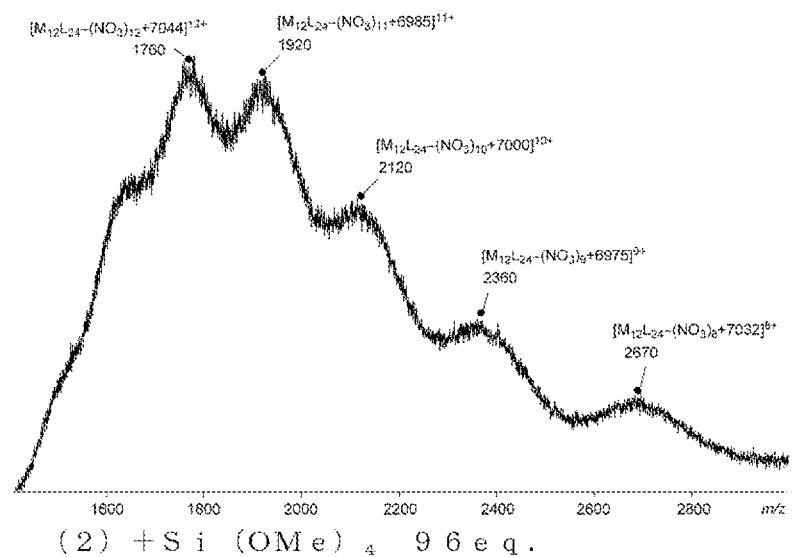
FIG. 6 is a view showing the CSI-MS spectrum of a silica nanoparticle-containing polyhedral complex obtained by adding TMOS in an amount of 96 equivalents based on a polyhedral complex (2a).
Figure 7:
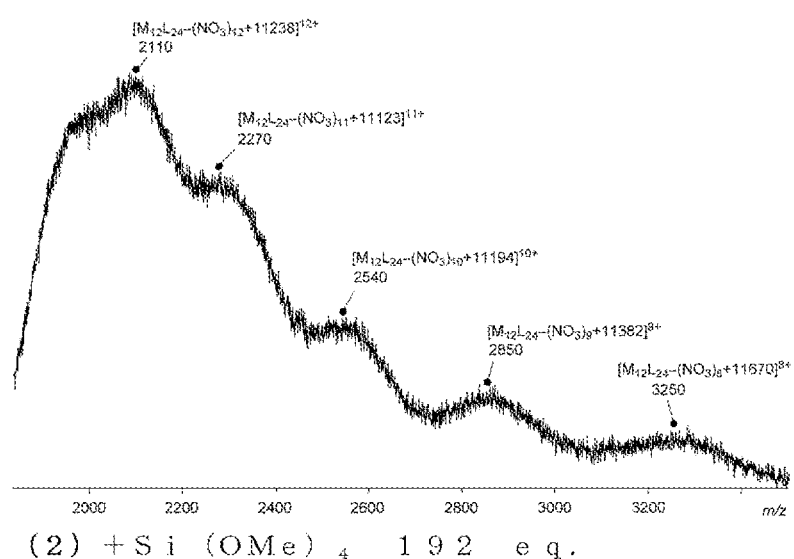
FIG. 7 is a view showing the CSI-MS spectrum of a silica nanoparticle-containing polyhedral complex obtained by adding TMOS in an amount of 192 equivalents based on a polyhedral complex (2a).

The silica nanoparticle-containing complex was subjected to cold-spray ionization mass spectrometry (CSI-MS). As shown in FIG. 5, a polyhedral complex containing silica having a molecular weight of about: 6000 Da was observed when adding TMOS in an amount of 72 equivalents. A polyhedral complex contained silica having a molecular weight of 7000 Da was observed when adding TMOS in an amount of 96 equivalents (see FIG. 6), and a polyhedral complex contained silica having a molecular weight of 11,200 Da was observed when adding TMOS in an amount of 192 equivalents (see FIG. 7). Specifically, it was confirmed that the silica nanoparticles were produced within the polyhedral complex. It was also found that the molecular weight of the silica nanoparticles produced can be controlled by changing the amount of TMOS.

It was found by laser desorption/ionization mass spectrometry (LDI-MS) that the molecular weight distribution of the silica nanoparticles was very narrow. The polydispersity of the nanoparticles was 1.007 to 1.008 independently of the amount of TMOS.

Examples 3 to 6

A DMSO solution (18.9 ml) of the polyhedral complex (2a) (14.6 μmol) obtained in Example 1 was diluted with water (75 μl) and chloroform (166 ml). After the addition of TMOS (63 equivalents (Example 3), 85 equivalents (Example 4), 130 equivalents (Example 5), or 170 equivalents (Example 6) based on the polyhedral complex), the mixture was condensed at room temperature for 4 days.

The reaction was tracked by $^1$H-NMR analysis. It was confirmed that a signal attributed to the polyhedral complex became significantly broad in the same manner as in Example 2. This suggests that silica nanoparticles were produced within the polyhedral complex.

After TMOS was completely hydrolyzed, the product was analyzed by $^1$H-NMR, DOSY-NMR, LDI-MS, and CSI-MS, and observed using an atomic force microscope (AFM).

After removing chloroform from the reaction mixture, using an evaporator, ethyl acetate and diethyl ether were added to the residue to obtain a light yellow precipitate. The precipitate was washed with methanol to obtain a silica nanoparticle-containing complex. The silica nanoparticle-containing complex was subjected to $^{29}$Si-MAS-NMR analysis and X-ray fluorescence (XRF) analysis.

Figure 8:
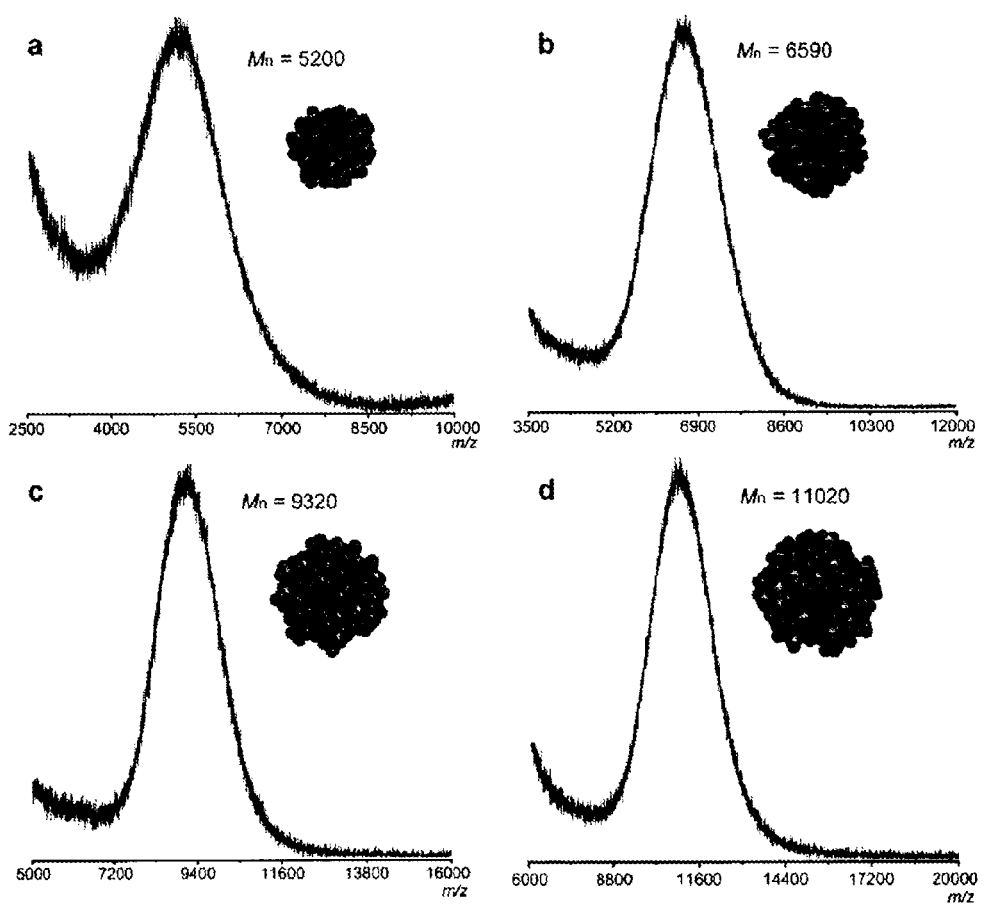
FIG. 8 is a view showing the LDI-MS spectrum of a silica nanoparticle-containing polyhedral complex obtained by adding TMOS in an amount of 65, 85, 130, or 170 equivalents based on a polyhedral complex (2a).

The DOSY-NMR, CSI-MS, LDI-MS, $^{29}$Si-MAS-NMR, and XRF analysis results are given below. FIG. 8 shows the LDI-MS spectrum. In FIG. 8, a indicates the LDI-MS spectrum of the silica nanoparticle-containing complex obtained in Example 3, b indicates the LDI-MS spectrum of the silica nanoparticle-containing complex obtained in Example 4, c indicates the LDI-MS spectrum of the silica nanoparticle-containing complex obtained in Example 5, and d indicates the LDI-MS spectrum of the silica nanoparticle-containing complex obtained in Example 6.

Example 3

Silica Nanoparticle-Containing Complex Obtained Using TMOS in an Amount of 65 Equivalents Diffusion coefficient D=1.5×10$^{-10}$ m$^2$ s$^{-1}$ (DMSO-d$_6$:CDCl$_3$=1:9, 300 K) by $^1$H nuclei.

CSI-MS (NO$_3^-$ salt, DMSO:CHCl$_3$:CH$_3$CN:CH$_3$OH=1:50:20:4, M=2a+silica (5100 Da)): [M-8(NO$_3^-$)]$^{8+}$ 2430, [M-9(NO$_3^-$)]$^{9+}$ 2150, [M-10(NO$_3^-$)]$^{10+}$ 1930, [M-11(NO$_3^-$)]$^{11+}$ 1750, [M-12(NO$_3^-$)]$^{12+}$ 1605.

LDI-MS: M$_n$=5200, M$_w$=5270 (M$_w$/M$_n$=1.013).

$^{29}$Si-MAS-NMR (59.7 MHz, MAS rate=3 kHz): Q$_1$:Q$_2$:Q$_3$:Q$_4$=12:28:39:21 (−82.4, −91.5, −100.4, −109.2 ppm).

XRF analysis: Number of Si atoms per polyhedral complex (2a): 66 (Pd:Si=1:5.5).

Example 4

Silica Nanoparticle-Containing Complex Obtained Using TMOS in an Amount of 85 Equivalents Diffusion coefficient D=1.5×10$^{-10}$ (DMSO-d$_6$:CDCl$_3$=1:9, 300 K) by $^1$H nuclei.

CSI-MS (NO$_3^-$ salt, DMSO:CHCl$_3$:CH$_3$CN:CH$_3$OH=1:50:20:6, M=2a+silica (6400 Da)): [M-8(NO$_3^-$)]$^{8+}$ 2590, [M-9(NO$_3^-$)]$^{9+}$ 2290, [M-10(NO$_3^-$)]$^{10+}$ 2060, [M-11(NO$_3^-$)]$^{11+}$ 1870, [M-12(NO$_3^-$)]$^{12+}$ 1715.

LDI-MS: M$_n$=6590, M$_w$=6650 (M$_w$/M$_n$=1.009).

$^{29}$Si-MAS-NMR (59.7 MHz, MAS rate=3 kHz): Q$_1$:Q$_2$:Q$_3$:Q$_4$=8:29:41:22 (−81.7, −91.5, −101.0, −109.9 ppm).

XRF analysis: Number of Si atoms per polyhedral complex (2a): 83 (Pd:Si=1:6.9).

Example 5

Silica Nanoparticle-Containing Complex Obtained Using TMOS in an Amount of 130 Equivalents Diffusion coefficient $D=1.5\times10^{-10}$ m$^2$s$^{-1}$ (DMSO-d$_6$:CDCl$_3$=1:9, 300 K) by $^1$H nuclei.

CSI-MS (NO$_3^-$ salt, DMSO:CHCl$_3$:CH$_3$CN:CH$_3$OH=1:50:20:4, M=2a+silica (9000 Da)): [M-9(NO$_3^-$)]$^{9+}$ 2585, [M-10(NO$_3^-$)]$^{10+}$ 2320, [M-11(NO$_3^-$)]$^{11+}$ 2100, [M-12(NO$_3^-$)]$^{12+}$ 1920, [M-13(NO$_3^-$)]$^{13+}$ 1770.

LDI-MS: $M_n$=9320, $M_w$=9390 ($M_w/M_n$=1.008).

$^{29}$Si-MAS-NMR (59.7 MHz, MAS rate=3 kHz): Q$_1$:Q$_2$:Q$_3$:Q$_4$=6:27:42:24 (−82.4, −91.2, −100.7, −109.9 ppm).

XRF analysis: Number of Si atoms per polyhedral complex (2a): 124 (Pd:Si=1:10.3).

Example 6

Silica Nanoparticle-Containing Complex Obtained Using TMOS in an Amount of 170 Equivalents Diffusion coefficient $D=1.4\times10^{-10}$ m$^2$s$^{-1}$ (DMSO-d$_6$:CDCl$_3$=1:9, 300 K) by $^1$H nuclei.

CSI-MS (NO$_3^-$ salt, DMSO:CHCl$_3$:CH$_3$CN:CH$_3$OH=1:60:20:15, M=2a+silica (11200 Da)): [M-8(NO$_3^-$)]$^{8+}$ 3250, [M-9(NO$_3^-$)]$^{9+}$ 2830, [M-10(NO$_3^-$)]$^{10+}$ 2540, [M-11(NO$_3^-$)]$^{11+}$ 2280, [M-12(NO$_3^-$)]$^{12+}$ 2110.

LDI-MS: $M_n$=11020, $M_w$=11100 ($M_w/M_n$=1.007).

$^{29}$Si-MAS-NMR (59.7 MHz, MAS rate=3 kHz): Q$_2$:Q$_3$:Q$_4$=18:43:39 (−9.1.0, −100.5, −109.9 ppm).

XRF analysis: Number of Si atoms per polyhedral complex (2a): 166 (Pd:Si=1:13.8).

As is clear from the above results, it was found that the molecular weight of the silica nanoparticles produced can be controlled within the range of 5200 to 11100 Da by changing the amount of TMOS. In each case, the polydispersity ($M_w/M_n$) was 1.013 or less.

Example 7

Synthesis of Titanium Oxide Nanoparticle-Containing Complex

A DMSO solution (70 μl) of the polyhedral complex (2a) obtained in Example 1 was diluted with chloroform (0.63 ml). After the addition of Ti(OiPr)$_4$ (72 or 96 equivalents based on the polyhedral complex), the mixture was condensed at 4° C. for 1 day. The reaction was tracked by $^1$H-NMR analysis. As shown in FIG. 9, it was confirmed that a signal attributed to the polyhedral complex became significantly broad when the precursor had been completely hydrolyzed. This suggests that titanium oxide nanoparticles were produced within the polyhedral complex.

Example 8

Synthesis of M$_{12}$L$_{24}$ Polyhedral Transition Metal Complex (Polyhedral Complex (2b))

(1) Synthesis of 2-[2,6-bis(4-pyridylphenylethynyl)phenoxy]ethyl β-D-glucopyranoside (2)

[Chemical Formula 14]

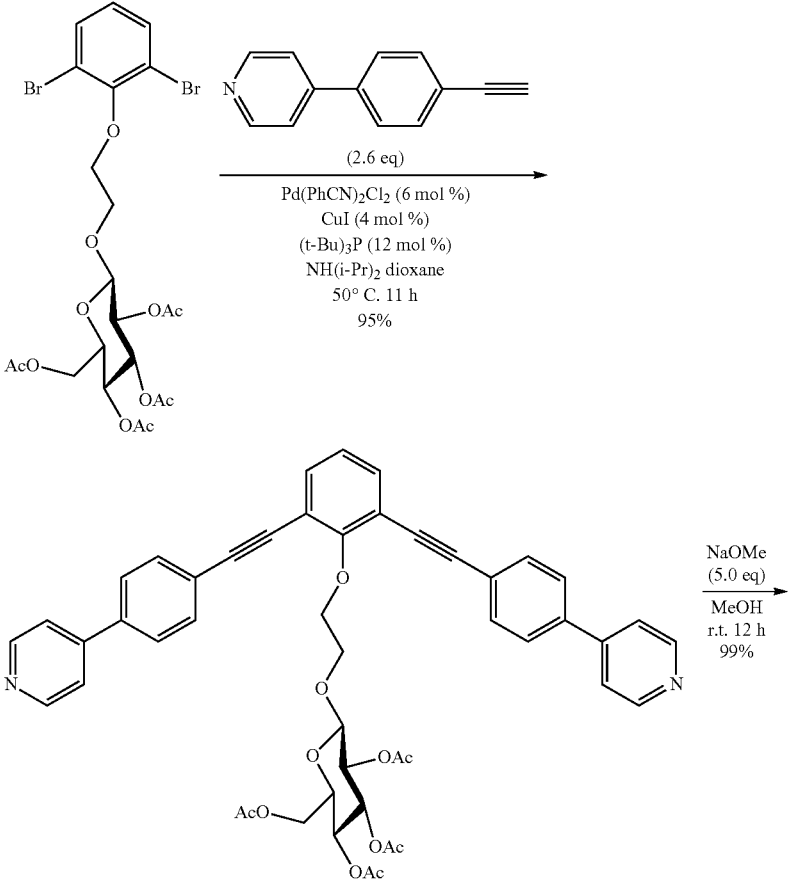

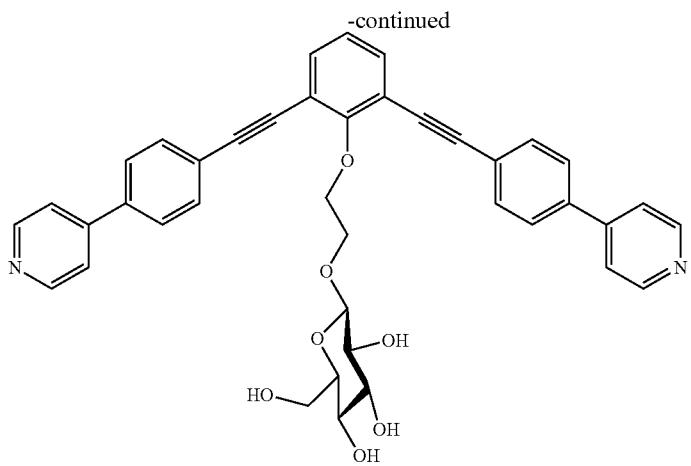

(i) Synthesis of 2-[2,6-bis(4-pyridylphenylethynyl)phenoxy]ethyl 2,3,4,6-tetra-O-acetyl-D-glucopyranoside Tri-t-butylphosphine (0.240 ml, 0.0960 mmol, 10% n-hexane solution) and diisopropylamine (0.80 ml, 5.6 mmol) were added to a 1,4-dioxane (7.0 ml) solution of 2-(2,6-dibromophenoxy)ethyl 2,3,4,6-tetra-O-acetyl-D-glucopyranoside (483 mg, 0.774 mmol) obtained in (i) in Example 1(1), 4-(4-pyridyl)phenylacetylene (360 mg, 2.01 mmol), $Pd(PhCN)_2Cl_2$ (17.8 mg, 0.0464 mmol), and cuprous iodide (5.9 mg, 0.031 mmol) in an argon atmosphere, and the mixture was stirred at 50° C. for 11 hours.

The reaction mixture was diluted with ethyl acetate (30 ml), and filtered. The filtrate was washed twice with water (40 ml), washed with a 5% ethylenediamine aqueous solution (30 ml), washed twice with water (40 ml), and washed with saturated saline (50 ml). The organic layer was dried over anhydrous sodium sulfate, and concentrated under reduced pressure. The residue was purified by silica gel column chromatography (eluant: chloroform:methanol=30:1 (volume ratio)) to obtain the target product as white crystals (607 mg, 0.738 mmol, yield: 95%). The melting point of the product was 70.8 to 72.0° C.

The $^1$H-NMR data, the $^{13}$C-NMR data, the IR data, and the elemental analysis and mass spectrometry (MALDI-TOFMS) results are given below.

$^1$H-NMR (500 MHz, CDCl$_3$, 27° C., δ ppm) 8.71 (d, j=6.2 Hz, 4H), 7.73-7.66 (m, 8H), 7.56 (d, j=4.8 Hz, 4H), 7.52 (d, j=7.8 Hz, 2H), 7.10 (t, j=7.8 Hz, 1H), 5.12 (t, j=9.5 Hz, 1H), 5.01 (t, j=9.4 Hz, 1H), 4.98 (t, j=9.5 Hz, 1H), 4.66 (d, j=8.0 Hz, 1H), 4.67-4.62 (m, 1H), 4.49-4.44 (m, 1H), 4.25-4.21 (m, 1H), 4.18-4.13 (m, 1H), 4.14-4.08 (m, 1H), 4.06-4.02 (m, 1H), 1.99 (s, 3H), 1.96 (s, 3H), 1.95 (s, 3H), 1.93 (s, 3H).

$^{13}$C-NMR (125 MHz, CDCl$_3$, 27° C., δ ppm) 170.6 (C), 170.2 (C), 169.4 (C), 169.3 (C), 161.0 (C), 150.5 (CH), 147.3 (C), 138.2 (C), 133.8 (CH), 132.3 (CH), 127.2 (CH), 124.0 (C), 123.6 (CH), 121.5 (CH), 117.2 (C), 101.3 (CH), 93.6 (C), 86.9 (C), 73.0 (CH$_2$), 72.8 (CH), 71.8 (CH), 71.3 (CH), 69.5 (CH$_2$), 68.4 (CH), 61.9 (CH$_2$), 20.63 (CH$_3$), 20.60 (CH$_3$), 20.58 (CH$_3$), 20.49 (CH$_3$).

IR (KBr; cm$^{-1}$) 2944, 2884, 1753, 1596, 1516, 1489, 1433, 1366, 1223, 1036, 907, 812, 681, 597.

Elemental analysis: Calcd for $C_{48}H_{42}N_2O_{11}$.0.5H$_2$O: C, 69.30; H, 5.21; N, 3.37.

Found: C, 69.26; H, 5.21; N, 3.39.

MALDI-TOFMS (matrix: CCA): Calcd for $C_{45}H_{43}N_2O_{11}$ ([M+H]$^+$) 823.3. Found: 823.5.

(ii) Synthesis of 2-[2,6-bis(4-pyridylphenylethynyl)phenoxy]ethyl β-D-glucopyranoside (2)

2-[2,6-Bis(4-pyridylphenylethynyl)phenoxy]ethyl 2,3,4,6-tetra-O-acetyl-D-glucopyranoside (532 mg, 0.647 mmol) and a methanol (60 ml) solution of sodium methoxide (174 mg, 3.22 mmol) were stirred at room temperature for 12 hours. The reaction mixture was neutralized with a sodium hydrogen carbonate aqueous solution, and concentrated under reduced pressure. The residue was washed with water, and dried to obtain 420 mg (0.642 mmol) of the target product as a white solid (yield: 99%). The melting point of the product was 184.2 to 185.3° C.

The $^1$H-NMR data, the $^{13}$C-NMR data, the IR data, and the elemental analysis and mass spectrometry (MALDI-TOFMS) results are given below.

$^1$H-NMR (500 MHz, DMSO-d$_6$, 27° C., δ ppm) 8.67 (d, j=6.4 Hz, 4H), 7.91 (d, j=8.5 Hz, 4H), 7.79-7.75 (m, 8H), 7.64 (d, j=8.2 Hz, 2H), 7.25 (t, j=7.8 Hz, 1H), 5.00-4.94 (m, 2H), 4.92-4.88 (m, 1H), 4.55-4.51 (m, 2H), 4.49-4.44 (m, 1H), 4.31 (d, j=7.6 Hz, 1H), 4.29-4.24 (m, 1H), 4.44-3.98 (m, 1H), 3.71-3.65 (m, 1H), 3.49-3.44 (m, 1H), 3.21-3.17 (m, 1H), 3.16-3.10 (m, 2H), 3.09-3.05 (m, 1H).

$^{13}$C-NMR (125 MHz, CDCl$_3$, 27° C., δ ppm) 60.6 (C), 150.3 (CH), 145.9 (C), 137.3 (C), 133.7 (CH), 132.1 (CH), 127.1 (CH), 124.3 (CH), 122.9 (C), 121.0 (CH), 116.8 (C), 103.1 (CH), 93.5 (C), 86.5 (C), 76.9 (CH), 76.8 (CH), 73.4 (CH), 73.1 (CH$_2$), 69.9 (CH), 67.8 (CH$_2$), 60.9 (CH$_2$).

IR (KBr, cm$^{-1}$) 2914, 2210, 1600, 1533, 1518, 1489, 1417, 1357, 1223, 1163, 1072, 1032, 1000, 914, 854, 812, 789, 750, 721, 682, 628, 566.

Elemental analysis: Calcd for $C_{40}H_{34}N_2O_7$.2H$_2$O: C, 69.55; H, 5.55; N, 4.06.

Found: C, 69.42; H, 5.73; N, 3.86.

MALDI-TOFMS (matrix: CCA): Calcd for $C_{40}H_{35}N_2O_7$ ([M+H]$^+$) 655.2. Found: 655.4.

(2) Synthesis of $M_{12}L_{24}$ Polyhedral Transition Metal Complex (Polyhedral Complex (2b))

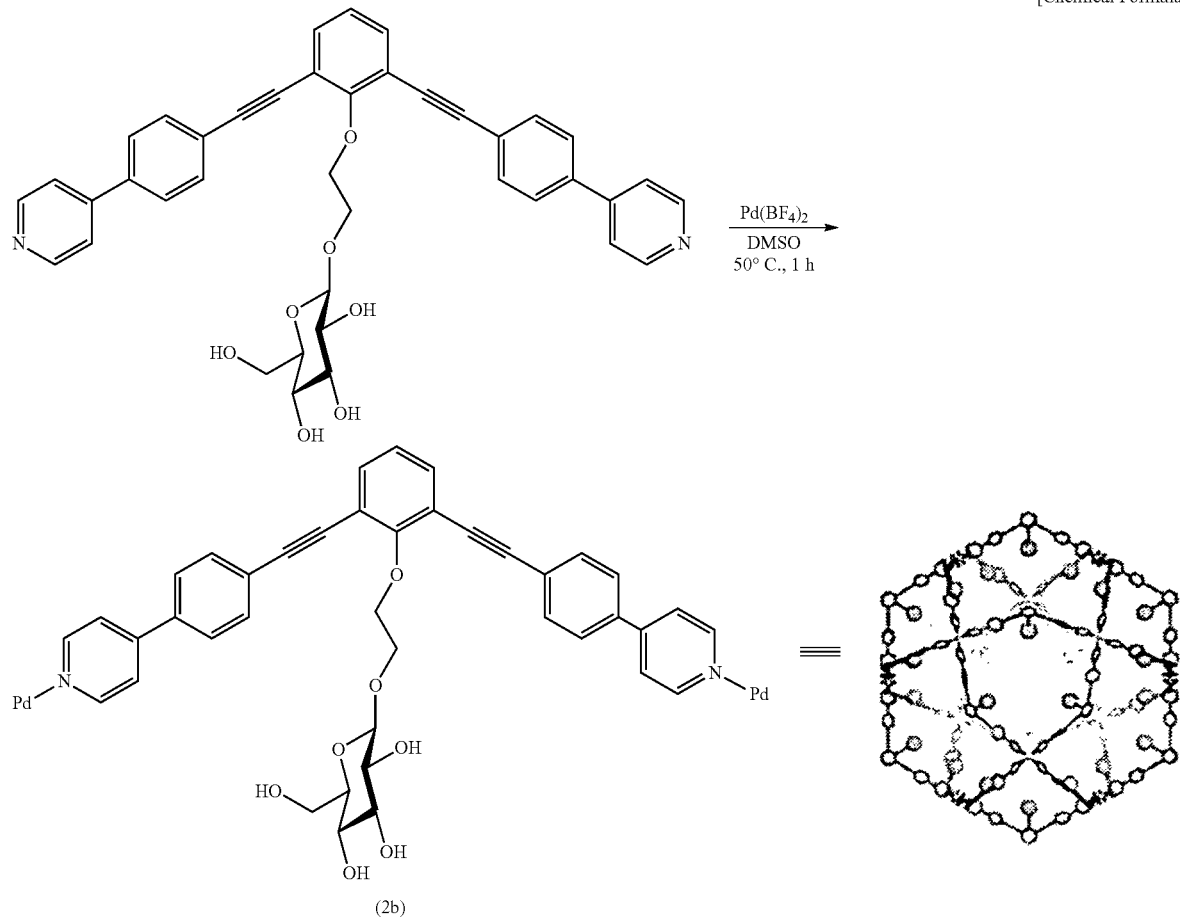

[Chemical Formula 15]

The glucopyranoside (2) (65.5 mg, 0.100 mmol) obtained in (1) was added to a DMSO solution of $Pd(BF_4)_2(CH_3CN)_4$ (10 mM, 5.1 ml), and the mixture was stirred at 50° C. for 1 hour.

It was confirmed by $^1$H-NMR analysis and CSI-MS analysis that the polyhedral complex (2b) was obtained quantitatively.

A white solid precipitated when adding ethyl acetate and diethyl ether to the reaction mixture. The white solid was collected by filtration, washed with diethyl ether, and dried under vacuum to obtain the target complex (yield: 85%). The complex was decomposed at 250° C. when measuring the melting point.

The NMR data, the mass spectrometry results, the IR data, and the elemental analysis results for the polyhedral complex (2b) are given below.

$^1$H-NMR (500 MHz, DMSO-$d_6$, 27° C., δ ppm) 9.31 (br, 96H), 8.18 (br, 96H), 7.96 (br, 96H), 7.76 (br, 96H), 7.61 (br, 48H), 7.24 (br, 24H), 4.95 (br, 48H), 488 (br, 24H), 4.51 (br, 48H), 4.46 (br, 24H), 4.30 (d, j=7.6 Hz, 24H), 4.25 (br, 24H), 4.00 (br, 24H), 3.66 (br, 24H), 3.46 (br, 24H), 3.18 (br, 24H), 3.12 (br, 48H), 3.05 (br, 24H).

$^{13}$C-NMR (125 MHz, DMSO-$d_6$, 27° C. δ ppm) 160.7 (C), 15.1.0 (CH), 149.4 (C), 134.3 (C) 133.9 (CH), 132.2 (CH), 127.5 (CH), 124.6 (CH), 1.2-4.0 (CH), 116.6 (C), 103.1 (CH), 93.2 (C), 87.5 (C), 76.9 (CH), 76.7 (CH), 73.4 (CH), 73.3 ($CH_2$), 69.9 (CH), 67.8 ($CH_2$), 60.9 ($CH_2$) (one signal attributed to the aromatic ring overlapped another signal, and was not observed clearly).

Diffusion coefficient D=$2.6\times10^{-11}$ $m^2s^{-1}$ (DMSO-$d_6$, 300 K), $7.9\times10^{-11}$ $m^2s^{-1}$ (DMSO-$d_6$:CDCl$_3$=1:3, 300 K) by $^1$H nuclei.

CSI-MS (BF$_4^-$ salt, DMSO:CH$_3$CN=1:15): calcd for [M-7 (BF$_4^-$)]$^{8+}$ 2638.0. found 2638.5. calcd for [M-8 (BF$_4^-$)]$_{8+}$ 2297.4. found 2297.8. calcd for [M-9 (BF$_4^-$)]$^{9+}$ 2032.5. found 2032.7. calcd for [M-10 (BF$_4^-$)]$^{10+}$ 1820.6. found 1820.9. calcd for [M-11 (BF$_4^-$)]$^{11+}$ 1647.2. found 1647.5. calcd for [M-12 (BF$_4^-$)]$^{12+}$ 1502.7. found 1503.0. calcd for [M-13 (BF$_4^-$)]$^{13+}$ 1380.4. found 1380.7. calcd for [M-14 (BF$_4^-$)]$^{14+}$ 1275.6. found 1276.0.

IR (KBr, cm$^{-1}$) 2879, 2208, 1612, 1491, 1431, 1292, 1223, 1074, 1035, 821, 791, 698, 567.

Elemental analysis: Calcd for $C_{960}H_{816}N_{48}O_{168}B_{24}F_{96}Pd_{12}\cdot24DMSO\cdot40H_2O$: C, 56.45; H, 4.77; N, 3.06.

Found: C, 56.63; H, 5.12; N, 3.35.

Example 9

Synthesis of Silica Nanoparticle-Containing Complex

A DMSO solution (11.9 ml) of the polyhedral complex (2b) (4.17 μmol) obtained in Example 8 was diluted with water (67 μl), chloroform (35.7 ml), and nitric acid (2.0 μmol). After the addition of TMOS (500 equivalents (311 μl, 2.09 mmol) based on the polyhedral complex (2b)), the mixture was condensed at room temperature for 4 days.

The reaction was tracked by $^1$H-NMR analysis. It was confirmed that a signal attributed to the polyhedral complex became significantly broad. This suggests that silica nanoparticles were produced within the polyhedral complex.

After TMOS was completely hydrolyzed, the product was analyzed by $^1$H-NMR, DOSY-NMR, and LDI-MS.

After removing chloroform from the reaction mixture using an evaporator, ethyl acetate and diethyl ether were added to the residue to obtain a Light yellow precipitate. The precipitate was washed with methanol to obtain a silica nanoparticle-containing complex. The silica nanoparticle-containing complex was subjected to $^{29}$Si-MAS-NMR analysis.

Figure 10:
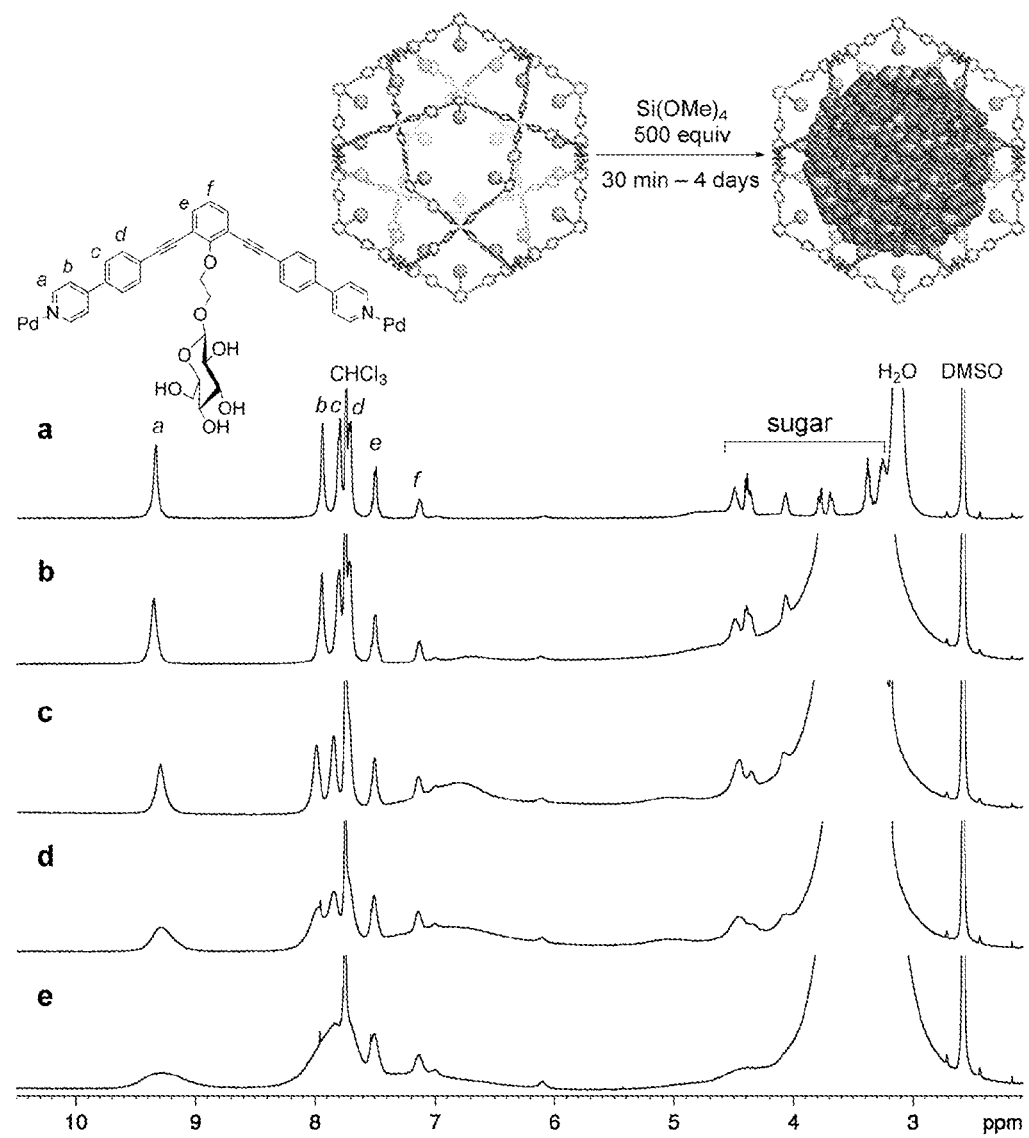
FIG. 10 is a view showing the $^1$H-NMR spectrum during production of a silica nanoparticle-containing complex of Example 8.
Figure 11:
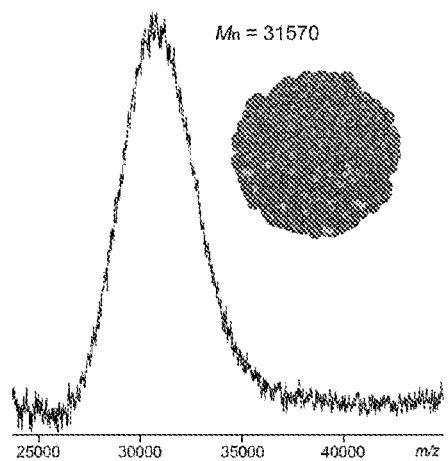
FIG. 11 is a view showing the LDI-MS spectrum of a silica nanoparticle-containing polyhedral complex obtained by adding TMOS to a polyhedral complex (2b).

The DOSY-NMR, LDI-MS, and $^{29}$Si-MAS-NMR data is given below. FIG. 10 shows the $^1$H-NMR spectrum, and FIG. 11 shows the LDI-MS spectrum.

In FIG. 10, a indicates the $^1$H-NMR spectrum of the silica nanoparticle-containing complex before the condensation reaction occurred, b indicates the $^1$H-NMR spectrum of the silica nanoparticle-containing complex when 30 minutes had elapsed after the condensation reaction occurred, c indicates the $^1$H-NMR spectrum of the silica nanoparticle-containing complex when 4 hours had elapsed after the condensation reaction occurred, d indicates the $^1$H-NMR spectrum of the silica nanoparticle-containing complex when 1 day had elapsed after the condensation reaction occurred, and e indicates the $^1$H-NMR spectrum of the silica nanoparticle-containing complex when 4 days had elapsed after the condensation reaction occurred.

As shown in FIG. 10, a signal attributed to the polyhedral complex became broad as TMOS contained in the silica nanoparticle-containing complex was hydrolyzed, and the condensation reaction proceeded.

Diffusion coefficient D=8.1×10$^{-11}$ m$^2$s$^{-1}$ (DMSO-d$_6$: CDCl$_3$=1:3, 300 K) by $^1$H nuclei.

LDI-MS: $M_n$=31570, $M_w$=31690 ($M_w/M_n$=1.004).

$^{29}$Si-MAS-NMR (59.7 MHz, MAS rate=3 kHz): $Q_2$:$Q_3$:$Q_4$=7:50:43 (−91.2, −100.4, −109.2 ppm).

As is clear from the results of Examples 2 to 6 and 9, it was found that the size (molecular weight) of the silica nanoparticles produced can be controlled by adjusting the size of the polyhedral complex. In each case, the polydispersity ($M_w/M_n$) was 1.013 or less.

<Transmission Electron Microscope (TEM) Observation>

Figure 12:
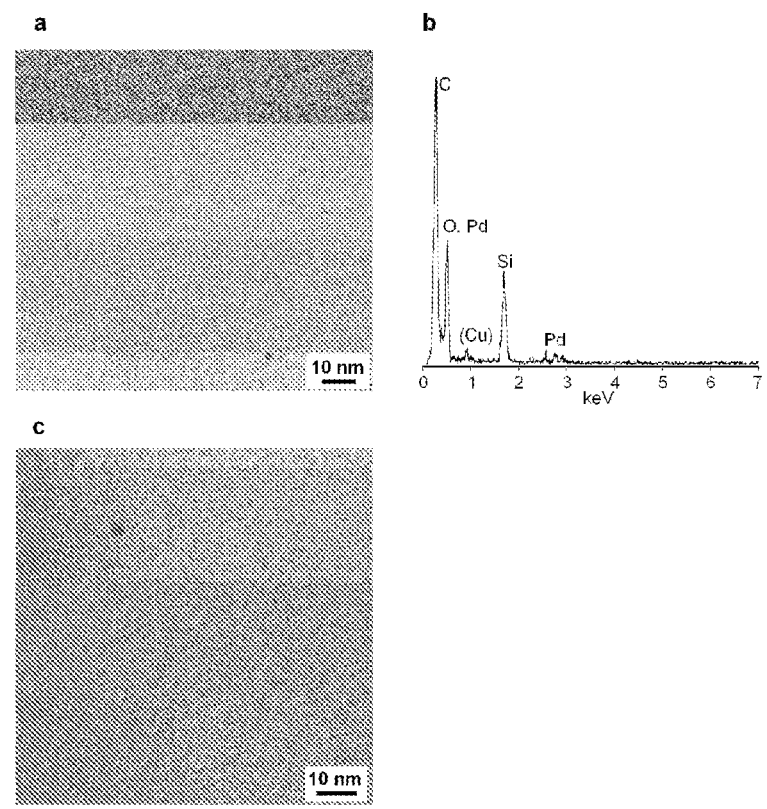
FIG. 12 is a view showing a transmission electron microscope (TEM) image and the energy-dispersive X-ray spectroscopy (EDS) spectrum of a silica nanoparticle-containing complex.

FIG. 12 shows a TEM image of the silica nanoparticle-containing complex.

In FIG. 12, a indicates a TEM image of the silica nanoparticle-containing complex obtained in Example 6, b indicates the EDS (energy-dispersive X-ray spectroscopy) spectrum of the silica nanoparticle-containing complex obtained in Example 6, and c indicates a TEM image of the silica nanoparticle-containing complex obtained in Example 9.

In FIG. 11(b), an Si atom and a Pd atom were observed (note that Cu is derived from the TEM sample grid).

The average diameter of the silica nanoparticles included in the complex was 4.0 nm.

INDUSTRIAL APPLICABILITY

The metal oxide particles included in the ultrafine particle-containing transition metal complex according to the invention are ultrafine particles having a uniform size (several nanometers), and the ultrafine particle-containing transition metal complex may be used in various applications such as a polishing agent, a coating agent, and a catalyst carrier.

The invention claimed is:

1. A polyhedral transition metal complex comprising a hollow shell, the hollow shell including n2, where n2 is 6, 12, 24, 30, or 60, transition metal atoms and 2(n2) bidentate organic ligands, the transition metal atoms being one type of transition metal atom selected from the group consisting of Ti, Fe, Co, Ni, Cu, Zn, Ru, Rh, Pd, Cd, Os, Ir, and Pt, and the bidentate organic ligands being compounds shown by a formula (I-1a), and formed so that the group derived from the polyhydroxy compound is oriented toward an inner space of the hollow shell,

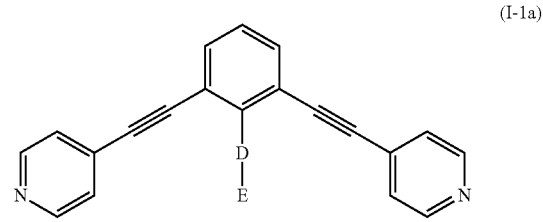

(I-1a)

wherein

D is at least one linking group selected from the group consisting of —O—, —C(=O)— and —(CH$_2$)$_S$—, where s is an integer from 1 to 20, E represents a group derived from a polyhydroxy compound by removal of a hydroxyl group and replaced with an —O— group which is attached to the linking group D, wherein said polyhydroxy compound is selected from the group consisting of a glycol, a glycol compound, a sugar, and a group derived form a polyhydroxy compound selected from the group consisting of a glycol, a glycerol compound and a sugar which have some or all of their hydrogen atoms replaced with a group selected from the group consisting of an alkyl group, a substituted or unsubstituted phenyl group, and an acyl group.

2. An ultrafine particle-containing transition metal complex comprising the polyhedral transition metal complex according to claim 1, and ultrafine particles of a metal oxide, the ultrafine particles being included within the hollow shell of the polyhedral transition metal complex.

3. The ultrafine particle-containing transition metal complex according to claim 2, wherein the metal oxide is silicon oxide, titanium oxide, zirconium oxide, aluminum oxide, or boron oxide.

4. The ultrafine particle-containing transition metal complex according to claim 2, wherein the metal oxide has a (weight average molecular weight)/(number average molecular weight) ratio of 1 to 1.05.

5. A method of producing the ultrafine particle-containing transition metal complex according to claim 2, the method comprising a step of adding a specific amount of a metal alkoxide to a solution of the polyhedral transition metal complex.

6. The method according to claim 5, wherein the metal alkoxide is a compound shown by $(R^5)_a M^1(OR^6)_b$, wherein $M^1$ represents a silicon atom, a titanium atom, a zirconium atom, an aluminum atom, or a boron atom, $R^5$ represents an alkyl group having 1 to 6 carbon atoms, $R^6$ represents an alkyl group having 1 to 6 carbon atoms that may be substituted with an alkoxy group having 1 to 6 carbon atoms, a is 0, 1, or 2, b is 2, 3, or 4, and a value "a+b" is a valence of $M^1$.

7. The method according to claim 5, wherein the metal alkoxide is added in an amount of 72 to 500 mol per mol of the polyhedral transition metal complex.

8. The method according to claim 5, wherein a molecular weight of the ultrafine particles of the metal oxide is controlled by changing the amount of the metal alkoxide added to the solution.

9. The polyhedral transition metal complex according to claim 1, wherein the transition metal atoms are Ru, Pd, or Pt.

10. The polyhedral transition metal complex according to claim 1, wherein said polyhydroxy compound is selected from the group consisting of a glycol, a glycerol compound, and a sugar.

* * * * *